United States Patent
Bringe et al.

(10) Patent No.: US 10,231,400 B2
(45) Date of Patent: Mar. 19, 2019

(54) INCREASED ALPHA-PRIME BETA-CONGLYCININ SOYBEANS

(71) Applicant: Monsanto Technology LLC, St. Louis, MO (US)

(72) Inventors: Neal Bringe, St. Louis, MO (US); Jonathan Jenkinson, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/582,047

(22) Filed: Apr. 28, 2017

(65) Prior Publication Data

US 2017/0231176 A1    Aug. 17, 2017

Related U.S. Application Data

(62) Division of application No. 14/702,887, filed on May 4, 2015, now Pat. No. 9,668,502, which is a division of application No. 12/199,410, filed on Aug. 27, 2008, now Pat. No. 9,049,823.

(60) Provisional application No. 60/971,336, filed on Sep. 11, 2007.

(51) Int. Cl.
| | |
|---|---|
| *A01H 5/10* | (2018.01) |
| *A01H 6/54* | (2018.01) |
| *G01N 33/68* | (2006.01) |
| *A23J 3/16* | (2006.01) |
| *A23L 11/00* | (2016.01) |

(52) U.S. Cl.
CPC ............... *A01H 5/10* (2013.01); *A01H 6/542* (2018.05); *A23J 3/16* (2013.01); *A23L 11/00* (2016.08); *A23L 11/03* (2016.08); *G01N 33/68* (2013.01)

(58) Field of Classification Search
None
See application file for complete search history.

(56) References Cited

U.S. PATENT DOCUMENTS

| | | | |
|---|---|---|---|
| 4,992,375 | A | 2/1991 | Wright |
| 5,015,580 | A | 5/1991 | Christou et al. |
| 5,024,944 | A | 6/1991 | Collins et al. |
| 5,416,011 | A | 5/1995 | Hinchee et al. |
| 6,864,362 | B2 | 3/2005 | Kinney |
| 2004/0037905 | A1 | 2/2004 | Bringe |
| 2007/0067871 | A1 | 3/2007 | Wu et al. |
| 2007/0224335 | A1 | 9/2007 | Wu et al. |
| 2011/0252490 | A1 | 10/2011 | Jenkinson |

FOREIGN PATENT DOCUMENTS

| | | |
|---|---|---|
| WO | 00/19839 A2 | 4/2000 |
| WO | 2006/034472 A1 | 3/2006 |
| WO | 2007030429 A2 | 3/2007 |

OTHER PUBLICATIONS

Adams et al., "Dietary Soy b-Conglycinin (7S Globulin) Inhibits Atherosclerosis in Mice", The Journal of Nutrition, 2003, pp. 511-516, vol. 134.

Agui et al., "Isolation and Characterization of a New Opioid Peptide Soymorphin Derived From Soy. BETA-Conglycinin", Peptide Science, 2005, pp. 195-198.

Allard, Principles of Plant Breeding, John Wiley & Sons, NY, pp. 50-98, 1960.

Baba et al., "Effects of Soybean Beta-Conglycinin on Body Fat Ratio and Serum Lipid Levels in Healthy Volunteers of Female University Students", Journal of Nutritional Science and Vitaminology, 2004, pp. 26-31, vol. 50.

Beilinson et al., "Genomic Organization of Glycinin Genes in Soybeans", Theoretical and Applied Genetics, 2002, pp. 1132-1140, vol. 104.

Boerma et al., "Pollen Movement Within and Between Rows to Male-Sterile Soybean", Crop Science., 1975, pp. 358-861, vol. 15.

Brim et al., Application of Genetic Male Sterility to the Recurrent Selection Scheme in Soybean, Crop Sci., 1973, pp. 528-530, vol. 13.

Chen et al., "Four Genes Affecting Seed Traits in Soybeans Map to Linkage Group F", The Journal of Heredity, 1998, pp. 211-215, vol. 89, No. 3.

Chrispeels et al., "Assembly of Storage Protein Oligomers in the Endoplasmic Reticulum and Processing of the Polypeptides in the Protein Bodies of Developing Cotyledons", The Journal of Cell Biology, 1982, pp. 306-313, vol. 93.

Christianson et al., "A Morphogenetically Competent Soybean Suspension Culture", Science, 1983, pp. 332-634, vol. 222.

Diers et al., "Genetic Mapping of the Gy4 and the Gy5 Glycinin Genes in Soybean and the Analysis of a Variant of Gy4", Theoretical and Applied Genetics, 1993, pp. 297-304, vol. 89.

Duranti et al., "The μ' Subunit From Soybean 7S Globulin Lowers Plasma Lipids and Upregulates Liver b-VLDL Receptors in Rats Fed a Hypercholesterolemic Diet", The Journal of Nutrition, 2004, pp. 1334-1339, vol. 134.

Fehr, "Principles of Cultivar Development" vol. 1 Theory and Technique and vol. 2 Crop Species, Soybean, 1987,pp. 360-376, Published by Macmillian Publishing Company, New York, Iowa State University.

(Continued)

Primary Examiner — Eileen B O Hara
(74) Attorney, Agent, or Firm — Thompson Coburn LLP; William A. Holtz; Chunping Li

(57) ABSTRACT

The invention overcomes the deficiencies of the art by providing a soybean plant with non-transgenic mutations conferring decreased α-subunit of β-conglycinin content and increased α'-subunit content of β-conglycinin in seed. Moreover, the invention provides an agronomically elite soybean plant with non-transgenic mutations conferring a gyclinin null phenotype, increased β-conglycinin content, and increased α'-subunit content of β-conglycinin in the seed. The invention also provides derivatives, and plant parts of these plants and uses thereof. Methods for producing such plants are also provided.

10 Claims, 1 Drawing Sheet

(56) References Cited

OTHER PUBLICATIONS

Fehr, "Breeding Methods for Cultivar Development", Soybeans: Improvement, Production and Uses, 2nd Edition, Agronomy Monograph, 1987, pp. 249 and 259, No. 16.

Finer et al., "Soybean Transformation: Technologies and Progress", Soybean: Genetics, Molecular Biology and Biotechnology, 1996, pp. 250-251, CAB Intl., Verma and Shoemaker (ed), Wallingford, Oxon, UK.

Hara et al., "Mechanism of Inducing Satiety Effects by Peptides Derived from Soybean beta-Conglycinin", Soy Protein Research, 2004, pp. 108-113, vol. 7.

Hartweck et al., "Auxin-Orientation Effects on Somatic Embryogenesis from Immature Soybean Cotyledons", In Vitro Cellular & Developmental Biology, 1988, pp. 821-828, vol. 24, No. 8.

Kohno et al., "Decreases in Serum Triacylglycerol and Visceral Fat Mediated by Dietary Soybean b-Conglycinin", Journal of Atherosclerosis and Thrombosis, 2006, pp. 247-255, vol. 13, No. 5.

Ladin et al., "Development Regulation of b-Conglycinin in Soybean Axes and Cotyledons", Plant Physiology, 1987, pp. 35-41, vol. 84.

Manzoni et al., "Soybean Protein Products as Regulators of Liver Low-Density Lipoprotein Receptors. II. µ-µ' Rich Commercial Soy Concentrate and µ' Deficient Mutant Differently Affect Low-Density Lipoprotein Receptor Activation", Journal of Agricultural Food Chemistry, 1998, pp. 2481-2484, vol. 46.

Manzoni et al., "Subcellular Localization of Soybean 7S Globulin in HepG2 Cells and LDL Receptor Up-Regulation by Its µ' Constituent Subunit", The Journal of Nutrition, 2003, pp. 2149-2155, vol. 133.

Maruyama et al., "Structure-Physicochemical Function Relationships of Soybean Beta-Conglycinin Constituent Subunits", J. Agric. Food Chem., 1999, pp. 5278-5284, vol. 47(12).

Maruyama et al., "The Effect of the N-Linked Glycans on Structural Features and Physiochemical Functions of Soybean beta-Conglycinin Homotrimers", Journal of the American Oil Chemists Society, 2002, pp. 139-144, vol. 79.

Moriyama et al., "Soybean b-Conglycinin Diet Suppresses Serum Triglyceride Levels in Normal and Genetically Obese Mice by Induction of b-Oxidation, Downregulation of Fatty Acid Synthase, and Inhibition of Triglyceride Absorption", Bioscience, Biotechnology, and Biochemistry, 2004, pp. 352-359, vol. 68, No. 2.

Moriyama et al., A Novel Enzyme-Linked Immunosorbent Assay for Quantification of Soybean beta-Conglycinin, a Major Soybean Storage Protein, in Soybean and Soybean Food Products, Journal of Nutritional Science and Vitaminology, 2005, pp. 34-39, vol. 51.

Nagano et al., "Dynamic Viscoelastic Study on the Gelation Properties of beta-Conglycinin-Rich and Glycinin-Rich Soybean Protein Isolates" Journal of Agricultural and Food Chemistry, 1996, pp. 3484-3488, vol. 44.

Nakamura et al., "The Stabilizing Behaviour of Soybean Soluble Polysaccharide and Pectin in Acidified Milk Beverages", International Dairy Journal, 2006, pp. 361-369, vol. 16.

Nakamura et al., "Molecular Biomedical Evaluation in Monkeys of Efficacy of Soy Products, Soy Protein, and Soy Isoflavone for Treatment of Hypercholesterolemia (Part 1)",Soy Protein Research, 2004, pp. 13-19, vol. 7.

Nakamura et al., Efficacy of Soy Product, Soy Protein or Soy Isoflavone, to Hypercholesterolemia and Osteoporosis: Its Molecular Biomedical Studies in Monkeys (Part II), Soy Protein Research, 2005, pp. 1-7, vol. 8.

Nielsen et al., "The Biochemistry and Cell Biology of Embryo Storage Proteins", Cellular and Molecular Biology of Plant Seed Development, 1997, pp. 151-220, Larkins and Vasil IK (Eds)., Kluwer Academic Publishers, Dordrecht, The Netherlands.

Nielsen et al., "Characterization of the Glycinin Gene Family in Soybean", Plant Cell, 1989, pp. 313-328, vol. 1, Issue 3.

Nishi et al., "Soybean b-Conglycinin Peptone Suppresses Food Intake and Gastric Emptying by Increasing Plasma Cholecystokinin Levels in Rats", The Journal of Nutrition, 2003, pp. 352-357, vol. 133.

Rickert et al., "Functional Properties of Improved Glycinin and Beta-Conglycinin Fractions", Journal of Food Science, 2004, pp. 303-311, vol. 69, No. 4.

Takahashi et al., "Accumulation of High Levels of Free Amino Acids in Soybean Seeds Through Integration of Mutations Conferring Seed Protein Deficiency", Planta, 2003, pp. 577-586, vol. 217.

Tezuka et al., "Properties of Tofu and Soy Milks Prepared From Soybean Having Different Subunits of Glycerin", Journal of Agricultural and Food Chemistry, 2000, pp. 1111-1117, vol. 48.

Tezuka et al., "Changes in Characters of Soybean Glycinin Groups I, IIa, and IIb Caused by Heating", Journal of Agricultural and Food Chemistry, 2004, pp. 1693-1699, vol. 52.

Tsukada et al., Genetic Analysis of Subunits of Two Major Storage Proteins (b-Conglycinin and Glycinin) in Soybean Seeds, Japan Journal of Breeding, 1986, pp. 390-400, vol. 36.

Utsumi, "Plant Food Protein Engineering", Advances in Food and Nutrition Research, Kinsella (Ed.), pp. 89-208, Academic Press, San Diego, CA, 1992.

Wright et al., "Plant Regeneration by Organogenesis of Glycine Max", Plant Cell Reports, 1986, pp. 150-154, vol. 5.

Yagasaki et al., "Biochemical Characterization of Soybean Protein Consisting of Different Subunits of Glycinin", J. Agric. Food Chem., 1997, pp. 656-660, vol. 45.

Yamauchi et al., "Molecular Understanding of Heat-Induced Phenomena of Soybean Protein", Food Review International, 1991, pp. 283-322, vol. 7.

Zuo et al., "Separation of Growth-Stimulating Peptides for Bifidobacterium From Soybean Conglycinin", World Journal of Gastroenterology, 2005, pp. 5801-5806, vol. 11, No. 37.

Fehr et al., "Genotype and Environment Influence on Protein Components of Soybean", Crop Science, 2003, pp. 511-514, vol. 43.

Abe et al., "Quantitative Difference of 7S Globulin on Vegetable Soybean Seeds", Journal of the Japanese Society for Food Science and Technology, 2005, pp. 107-113, vol. 52, No. 3.

Mahmoud et al., "Effect of Six Decades of Selective Breeding on Soybean Protein Composition and Quality: A Biochemical and Molecular Analysis", Journal of Agricultural Food Chemistry, 2006, pp. 3916-3922, vol. 54.

Yaklich, "?-Conglycinin and Glycinin in High-Protein Soybean Seeds", Journal of Agricultural Food Chemistry, 2001, pp. 729-735, vol. 49 Issue 2.

Krishnan et al., "Identification of Glycinin and Beta-Conglycinin Subunits that Contribute to the Increased Protein content of High-Protein Soybean Lines", Journal of Agricultural Food Chemistry, Feb. 1, 2007, pp. 1839-1845, vol. 55.

Carrao-Panizzi et al., "Genetic Variation and Environmental Effects on Beta-Conglycinin and Glycinin Content in Brazilian Soybean Cultivars", Pesquisa Agropecuaria Brasileira, 2008, pp. 1105-1114, vol. 43 No. 9.

Lopez-Tapia et al., "Detection of the Presence of Soya Protein in Milk Powder by Sodium Dodecyl Sulfate Capillary Electrophoresis", Journal of Chromatography A, Mar. 1999, pp. 153-160, vol. 836 Issue 1.

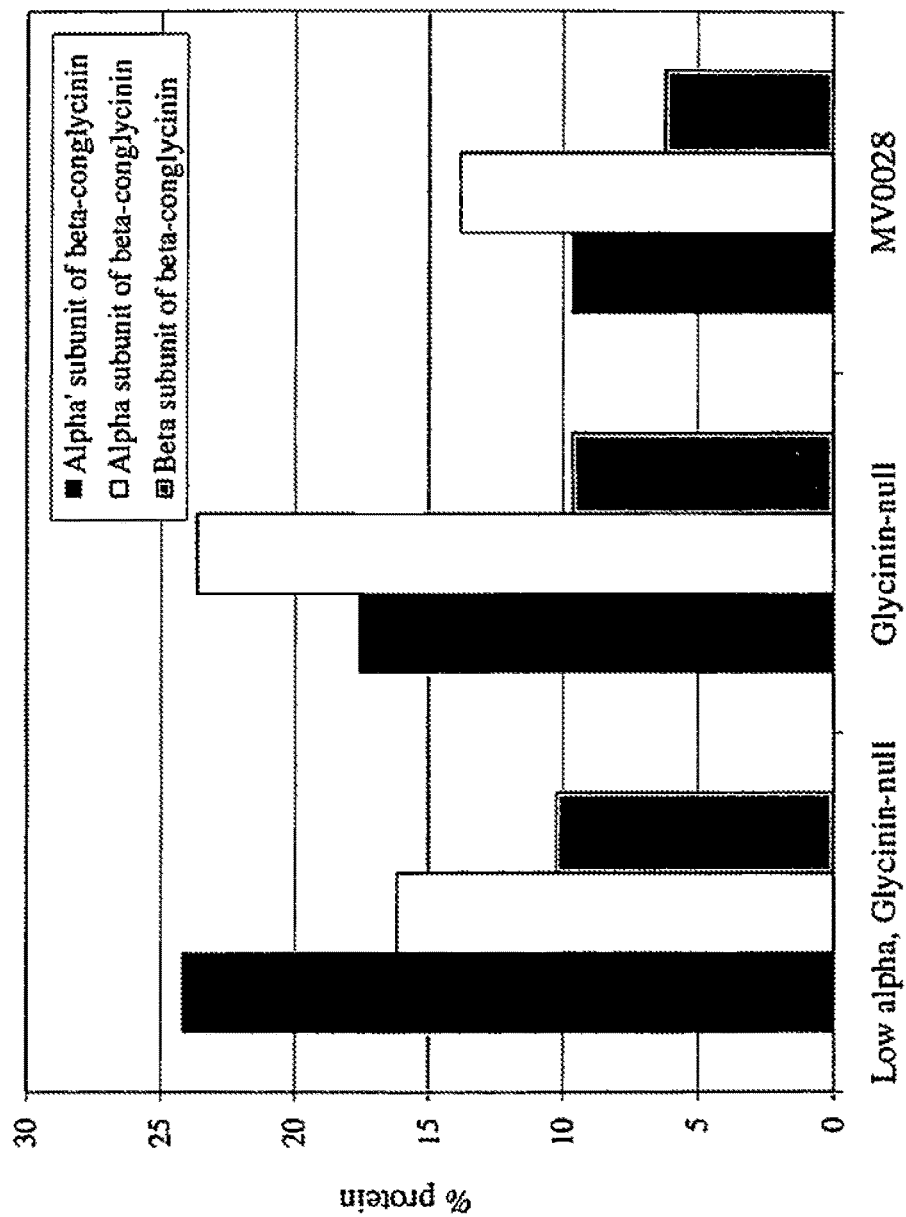

INCREASED ALPHA-PRIME BETA-CONGLYCININ SOYBEANS

CROSS-REFERENCE TO RELATED APPLICATIONS

This application is a divisional of U.S. patent application Ser. No. 14/702,887, filed May 4, 2015, which is a divisional of U.S. patent application Ser. No. 12/199,410, filed Aug. 27, 2008, which claims the benefit under 35 U.S.C. § 119(e) of U.S. Provisional Patent Application No. 60/971,336, filed Sep. 11, 2007, the entireties of which are hereby incorporated by reference.

BACKGROUND OF THE INVENTION

1. Field of the Invention

The present invention relates generally to the field of plant breeding and molecular biology. In particular, the invention relates to soybeans with increased α' subunit of β-conglycinin content and materials for making such plants.

2. Description of Related Art

Soybeans are primarily grown for protein and oil. Soybean accounts for approximately 69% of the 161 million metric tons (MMT) of major protein meals in world trade (USDA, 2008). In the United States, about 30MMT of soybean meal is consumed annually. Although soybeans produce a high quality cost-effective protein meal, there is a rising demand for increased nutritional value and functionality of the protein meal.

Composition and conformation are responsible for a protein's functionality. Compositional differences that could alter functionality include, for example, the ratio of protein fractions, variations in subunit concentrations within fractions, and differences in amino acid profiles. Soy proteins have four major water-extractable fractions (2S, 7S, 11S, and 15S) that can be isolated on the basis of their sedimentation coefficients. The 7S (β-conglycinin) and 11S (glycinin) proteins represent the majority of the fractions within the soybean.

Glycinin (11s globulin) is composed of five different subunits, designated A1aB2, A2B1a, A1bB1b, A5A4B3, A3B4, respectively. Each subunit is composed of two polypeptides, one acidic and one basic, covalently linked through a disulfide bond. The two polypeptide chains result from post-translational cleavage of proglycinin precursors; a step that occurs after the precursor enters the protein bodies (Chrispeels et al., 1982). Five major genes have been identified to encode these polypeptide subunits. They are designated as Gy1, Gy2, Gy3, Gy4 and Gy5, respectively (Nielsen et al., 1997). In addition, a pseudogene, gy6, and minor gene, Gy7, were also reported (Beilinson et al., 2002). Genetic mapping of these genes has been reported by various groups (Diers et al., 1993, Chen and Shoemaker 1998, Beilinson et al., 2002). Gy1 and Gy2 were located 3 kb apart and mapped to linkage group N (Nielsen et al., 1989), Gy3 was mapped to linkage group L (Beilinson et al., 2002). Gy4 and Gy5 were mapped to linkage groups O and F, respectively. In addition, B2G2 or "11S null" soybean variety has a unique seed composition including high level of β-conglycinin and low amount of glycinin. However, the B2G2 variety exhibits agronomically inferior characteristics such as low yield, excessive lodging and green seed. A number of breeding lines were developed, which carried all or parts of the mutations present in the B2G2 lines. Wu et al. provided breeding lines with agronomically acceptable characteristics (U.S. patent application Ser. No. 11/517,186).

β-conglycinin (7S), on the other hand, is composed of α (~67 kda), α' (~71 kDa) and β (~50 kDa) subunits and each subunit is processed by co- and post-translational modifications (Ladin et al., 1987; Utsumi, 1992). Cgy2, 3 encode the α-subunit. Genetic analysis indicated that Cgy2 is tightly linked to Cgy3, whereas Cgy1 segregates independently of the other two. Cgy1 encodes the α'-subunit (Tsukada et al., 1986). The relative percentages of α',α, and β chains in the trimer are ~35, 45, and 20% of total β-conglycinin, respectively (Maruyama et al., 1999).

Soy protein functionality is partly dependent on the β-conglycinin-to-glycinin ratio and variations in the subunit compositions, which can vary among genotypes. The differences in composition and structure between β-conglycinin and glycinin are exhibited in both nutritional and functional properties. Glycinins contain more methionine and cysteine per unit than β-conglycinins, however soybeans lacking glycinins and enriched in β-conglycinins can have similar levels of total sulfur amino acids as soybeans containing glycinins. Glycinins are important for forming the protein particles that make up firm tofu gels (Tezuka, et al., 2000), but weaker gels are formed in the absence of β-conglycinin than those formed in the absence of glycinins (Tezuka, et al., 2004). The gelling properties of β-conglycinins and of soy protein isolates made from soybeans enriched in β-conglycinins show advantages under some conditions that may apply to meat applications (Nagano, et al., 1996; Rickert, et al., 2004). The gelling properties of β-conglycinin can be altered by varying the subunit composition with the alpha-subunit showing advantages (Salleh, 2004). The solubility and emulsifying properties of β-conglycinin are good in part because of the hydrophilic extention regions of the α and α' subunits (Yamauchi et al., 1991, Mauryama et al., 2002). There is potential to create valuable soybeans and ingredients for food use having increased β-conglycinin levels and decreased glycinin levels.

β-conglycinin has significant potential to positively impact human health (Baba et al., 2004). In particular, β-conglycinin has been found to lower cholesterol, triglycerides and visceral fat. Kohno et al. demonstrated that a significant reduction in triglycerol levels and viseral fat in human subjects that consumed 5 g of β-conglycinin per day (Kohno et al. 2006). Similarly, Nakamura et al. found that β-conglycinin upregulates genes associated with lipid metabolism in a primate model (2005). In addition, Nakamura et al. showed β-conglycinin had a significant effect preventing bone mineral density loss (2006). In addition, β-conglycinin demonstrated effects in lowering serum insulin and blood sugar (Moriyama et al. 2005). Due to β-conglycinin effects on triglycerides, cholesterol, fat, insulin and sugar levels, it may play an important role in health programs. In addition, β-conglycinin inhibits artery plaque formation in mice and may have similar affects in human subjects as well (Adams et al. 2004).

Furthermore, β-conglycinin may have a significant effect on intestinal microflora in humans. β-conglycinin is inhibits growth of harmful baceteria, such as *E. coli*, while stimulating growth of beneficial bacteria, such as bifidobacteria, in a number of animal models (Nakamura et al. 2004, Zou et al. 2005,). β-conglycinin could be used both to reduce *E. coli* growth after infection and maintain a healthy intestinal microbial community.

The α' subunit of β-conglycinin may play a predominant role in many of the health benefits associated with β-conglycinin. A number of experiments using animal models have indicated that α' subunit from soybean β-conglycinin could lower plasma triglycerides, and also increase LDL ("bad" cholesterol) removal from blood (Durand et al., 2004, Moriyama et al., 2004, Adams et al., 2004, Nishi et al., 2003). Therefore, soybean varieties with an increased β-conglycinin content will have higher value than traditional varieties and will be suitable for use in nutrition drinks and other food products. In an attempt to identify the biologically active polypeptide(s), Manzoni et al. attempted to characterize biologically active polypeptides in β-conglycinin and indirectly demonstrated that the α'-subunit had a putative role in lowering cholesterol (Manzoni et al., 1998). Additionally, Manzoni et al. also demonstrated the influence of the α' subunit on the increase in LDL uptake and degradation and LDL receptor mRNA levels (Manzoni et al., 2003). Duranti et al. (2004) demonstrated that the α' subunit can lower triglycerides and plasma cholesterol in vivo.

The β-subunit of β-conglycinin has a number of health benefits as well. For instance, the β-subunit enhances satiety by causing cholecystokinin secretion (Takashi et al. 2003, Hara et al., 2004). Cholecystokinin is a peptide hormone of the gastrointestinal system responsible for stimulating the digestion of fat and protein. Cholecystokinin, previously called is synthesized by I-cells and secreted in the duodenum, the first segment of the small intestine, and causes the release of digestive enzymes and bile from the pancreas and gallbladder, respectively. It also acts as a hunger suppressant. Hence, β-subunit may suppress appetite and may play a role in an overall weight management program.

The β-subunit may have a function in mental health as well. Soymorphin-5 are released by digesting the β-subunit with pancreatic elastase and leucine aminopeptidase. Soymorphin-5 is an opioid peptide. Opioids are chemical substances that have a morphine-like action in the body. Opioids are primarily used for pain relief. These agents work by binding to opioid receptors, which are found principally in the central nervous system and the gastrointestinal tract. Soymorphin-5 demonstrated anxiolytic effect after oral administration on mice, which suggest the intake of β-subunit may decrease mental stress (Agui et al. 2005).

Thus, the present invention produces soybeans with increased levels of the α'-subunit of β-conglycinin. Methods and compositions are disclosed herein to obtain soybeans with desirable protein composition.

SUMMARY OF THE INVENTION

The present invention relates to increased α'-subunit and conserved β subunit composition of soybean seed which has improved physical and human health properties compared to commercial soybean protein ingredients. The current invention provides a soybean plant with non-transgenic traits conferring increased seed α'-subunit content phenotype. Thus, the plants of the current invention comprise, in one aspect, seeds with increased α'-subunit content phenotype. In certain embodiments, the seed α'-subunit content for plants of the invention is about or at least about 9, 10, 11, 12, 13, 14, 15, 16, 17, 18, 19, 20 percent or more of the total protein content. In sane embodiments, a plant of the invention has a seed α-subunit content of about or less than about 15, 14, 13, 12, 11, 10, 9, 8, 7, 6, 5, 4, 3, 2, 1, or 0 percent of the total protein. In further embodiments, a plant of the invention has a ratio of α-subunit content to α'-subunit of about 1.0, 0.9, 0.8, 0.7, 0.6, 0.5, 0.4, 0.3, 0.2, 0.1 or even 0, derivable therein.

The current invention provides, as a further embodiment, soybean plants capable of producing seeds with reduced glycinin content, increased seed β-conglycinin content and subsequently increased α'-subunit of β-conglycinin. Thus, the plants of the current invention comprise, in one aspect, seeds with reduced glycinin content, increased β-conglycinin content and α-subunit and α'-subunit of β-conglycinin. In some embodiments, a plant of the invention produces a seed comprising a seed glycinin content of about or less than about 18, 17, 16, 15, 14, 13, 12, 11, 10, 9, 8, 7, 6, 5, 4, 3, 2, 1, or 0 percent of the total seed protein. In certain embodiments, the plant of the current invention produces a seed comprising a seed β-conglycinin content of about or at least about 37, 38, 39, 40, 41, 42, 43, 44, 45, 46, 47, 48, 49, 50, 51, 52, 53, 54, 55, 56, 57, 58, 59, or 60 percent or more of the total seed protein. In another embodiment, the seed α'-subunit content for plants of the invention is about or at least about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 percent or more of the total seed protein content. In further embodiments, a plant of the invention has a seed α-subunit content of about or less than about 15, 14, 13, 12, 11, 10, 9, 8, 7, 6, 5, 4, 3, 2, 1, or 0 percent of the total seed protein. In still further embodiments, a plant of the invention is capable of producing a seed with a β-conglycinin content comprising an α-subunit and an α'-subunit in a ratio of about 1.0, 0.9, 0.8, 0.7, 0.6, 0.5, 0.4, 0.3, 0.2, 0.1 or even 0.

Plant parts are also provided by the invention. Parts of a plant of the invention include, but are not limited to, pollen, ovules, meristems, cells, and seed. Cells of the invention may further comprise, regenerable cells, such as embryos meristematic cells, pollen, leaves, roots, root tips, and flowers. Thus, these cells could be used to regenerate plants of the invention.

Also provided herein are parts of the seeds of a plant according to the invention. Thus, crushed seed, and meal or flour made from seed according to the invention is also provided as part of the invention. The invention further comprises, a method for making soy meal or flour comprising crushing or grinding seed according to the invention. Such soy flour or meal according to the invention may comprise genomic material of plants of the invention. In one embodiment, the food may be defined as comprising the genome of such a plant. In further embodiments soy meal or flour of the invention may be defined as comprising increased β-conglycinin and decreased glycinin content, as compared to meal or flour made from seeds of a plant with an identical genetic background, but not comprising the non-transgenic, mutant Gy3 and Gy4 null alleles.

In yet a further aspect of the invention there is provided a method for producing a soybean seed, comprising crossing the plant of the invention with itself or with a second soybean plant. Thus, this method may comprise preparing a hybrid soybean seed by crossing a plant of the invention with a second, distinct, soybean plant.

Still yet another aspect of the invention is a method of producing a food product for human or animal consumption comprising: (a) obtaining a plant of the invention; (b) cultivating the plant to maturity; and (c) preparing a food product from the plant. In certain embodiments of the invention, the food product may be protein concentrate, protein isolate, meal, flour or soybean hulls. In some embodiments, the food product may comprise beverages, infused foods, sauces, coffee creamers, cookies, emulsifying agents, bread, candy instant milk drinks, gravies, noodles, soynut butter, soy coffee, roasted soybeans, crackers, candies, soymilk, tofu, tempeh, baked soybeans, bakery ingredients, beverage powders, breakfast cereals, nutritional bars, meat or meat analogs, fruit juices, desserts, soft frozen products, confections or intermediate foods. Foods produced from the plants of the invention may comprise increased α'-subunit content and thus be of greater nutritional value foods made with typical soybean varieties In a further aspect of the invention is a method of producing a nutraceutical, comprising: (a) obtaining a plant of the invention; (b) cultivating the plant to maturity; and (c) preparing a nutraceutical from the plant. Products produced from the plants of the invention may comprise increased α'-subunit content and thus be of greater nutritional value foods made with typical soybean varieties. For example, products from soybean seeds with increased α'-sub unit may be used alone or combination with other mechanisms in a lipid-lowering therapy.

In further embodiments, a plant of the invention may further comprise a transgene. The transgene may in one embodiment be defined as conferring preferred property to the soybean plant selected from the group consisting of herbicide tolerance, increased yield, insect control, fungal disease resistance, virus resistance, nematode resistance, bacterial disease resistance, mycoplasma disease resistance, altered fatty acid composition, altered oil production, altered amino acid composition, altered protein production, increased protein production, altered carbohydrate production, germination and seedling growth control, enhanced animal and human nutrition, low raffinose, drought and/or environmental stress tolerance, altered morphological characteristics, increased digestibility, industrial enzymes, pharmaceutical proteins, peptides and small molecules, improved processing traits, improved flavor, nitrogen fixation, hybrid seed production, reduced allergenicity, biopolymers, biofuels, or any combination of these.

In certain embodiments, a plant of the invention may be defined as prepared by a method wherein a plant comprising non-transgenic mutations conferring increased α'-subunit content is crossed with a plant comprising agronomically elite characteristics. The progeny of this cross may be assayed for agronomically elite characteristics and α- and α'-subunit protein content, and progeny plants selected based on these characteristics, thereby generating the plant of the invention. Thus in certain embodiments, a plant of the invention may be produced by crossing a selected starting variety with a second soybean plant comprising agronomically elite characteristics. In some embodiments, a plant of the invention may be defined as prepared by a method wherein a plant comprising a non-transgenic mutation conferring a reduced glycinin content and an increased seed β-conglycinin content is crossed with a plant comprising increased α'-subunit content.

BRIEF DESCRIPTION OF THE DRAWINGS

FIG. 1: The percent of total protein of β-conglycinin α-, α'-, β-subunits in commercial variety MV0028, glycinin null line, and glycinin null+increased α'-subunit line.

DESCRIPTION OF ILLUSTRATIVE EMBODIMENTS

The present invention provides plants and methods for producing plants comprising non-transgenic mutations that confer seed with a β-conglycinin content comprising an increased α'-subunit level of β-conglycinin. Thus, plants of the invention are of great value as increased levels of α'-subunit of β-conglycinin within the seed provide improved nutritional characteristics and solubility of the soybean flour and protein isolates. Additionally, plants provided herein comprise agronomically elite characteristics, enabling a Commercially significant yield.

The invention also provides plants and methods for producing plants comprising non-transgenic mutations that confer increased β-conglycinin and reduced glycinin. The combination of increased β-conglycinin and increased α'-subunit phenotype provides an increased content of the highly functional and healthful α'-subunit of β-conglycinin protein.

I. Plants of the Invention

The invention provides, for the fust time, plants and derivatives thereof of soybean that combine non-transgenic mutations conferring increased α'-subunit content. In certain embodiments, the α'-subunit content of the seeds of plants of the invention may be greater than about 9, 10, 11, 12, 13, 14, 15, 16, 17, 18, 19 or even 20% of the total seed protein. In other embodiments, the glycinin content of the seeds of the plants of the invention maybe about or less than about 15, 14, 13, 12, 11, 10, 9, 8, 7, 6, 5, 4, 3, 2, 1, or 0 percent of the total seed protein, the β-conglycinin content of the seeds of the plants of the invention maybe about or at least about 34, 35, 36, 37, 38, 39, 40, 41, 42, 43, 44, 45, 46, 47, 48, 49, 50 percent or more of the total protein content, the α'-subunit content of the seeds of the plant of the invention maybe about or at least about 9, 10, 11, 12, 13, 14, 15, 16, 17, 18, 19, 20, 21, 22, 23, 24, 25, 26, 27, 28, 29, 30, 31, 32, 33,. 34, 35, 36, 37, 38, 39, 40 percent or more and the α-subunit content of the seeds of the plants of the invention are about or less than about 15, 14, 13, 12, 11, 10, 9, 8, 7, 6, 5, 4, 3, 2, 1, or 0 percent of the total protein. In still further embodiments, a seed of the plant of the invention has β-conglycinin content comprising an α-subunit and an α'-subunit in a ratio of about 1.0, 0.9, 0.8, 0.7, 0.6, 0.5, 0.4, 0.3, 0.2, 0.1 or even 0.

One aspect of the current invention is therefore directed to the aforementioned plants and parts thereof and methods for using these plants and plant parts. Plant parts include, but are not limited to, pollen, an ovule and a cell. The invention further provides tissue cultures of regenerable cells of these plants, which cultures regenerate soybean plants capable of expressing all the physiological and morphological characteristics of the starting variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the starting plant variety from which the regenerable cells were obtained.

II. Production of Soybean Varieties with Increased α'-Subunit Content

The present invention describes methods to produce soybean plants with increased α'-subunit protein content in seed. Certain aspects of the invention also provide methods for selecting parents for breeding of plants with increased α'-subunit protein content in seed. One method involves screening germplasm for α'-subunit and α-subunit content in soybean seed. Another method includes evaluating the pedigree of potential parents for PI88788 in its lineage that may carry the increased α'-subunit trait.

Certain aspects of the invention also provide methods for breeding of plants that enable the introduction of non-transgenic increased α'-subunit traits into a heterologous soybean genetic background. In general, breeding techniques take advantage of a plant's method of pollination. There are two general methods of pollination: self-pollination which occurs if pollen from one flower is transferred to the same or another flower of the same plant, and cross-pollination which occurs if pollen comes to it from a flower on a different plant. Plants that have been self-pollinated and selected for type over many generations become homozygous at almost all gene loci and produce a uniform population of true breeding progeny, homozygous plants.

In development of suitable varieties, pedigree breeding may be used. The pedigree breeding method for specific traits involves crossing two genotypes. Each genotype can have one or more desirable characteristics lacking in the other, or, each genotype can complement the other. If the two original parental genotypes do not provide all of the desired characteristics, other genotypes can be included in the breeding population. Superior plants that are the products of these crosses are selfed and are again advanced in each successive generation. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. A selfed generation (S) may be considered to be a type of filial generation (F) and may be named F as such. After at least five generations, the inbred plant is considered genetically pure.

Each breeding program should include a periodic, objective evaluation of the efficiency of the breeding procedure. Evaluation criteria vary depending on the goal and objectives. Promising advanced breeding lines are thoroughly tested and compared to appropriate standards in environments representative of the commercial target area(s) for generally three or more years. Identification of individuals that are genetically superior is difficult because genotypic value can be masked by confounding plant traits or environmental factors. One method of identifying a superior plant is to observe its performance relative to other experimental plants and to one or more widely grown standard varieties. Single observations can be inconclusive, while replicated observations provide a better estimate of genetic worth.

Mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Descriptions of other breeding methods that are commonly used for different traits and crops can be found in one of several reference books (e.g., Allard, 1960; Simmonds, 1979; Sneep et al., 1979; Fehr, 1987a,b).

The effectiveness of selecting for genotypes with traits of interest (e.g., increased yield, disease resistance, fatty acid profile) in a breeding program will depend upon: 1) the extent to which the variability in the traits of interest of individual plants in a population is the result of genetic factors and is thus transmitted to the progenies of the selected genotypes; and 2) how much the variability in the traits of interest among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits such as yield is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregates or superior genotypes with the traits of interest is extremely difficult and its success is dependent on the plant breeder's ability to minimize the environmental variation affecting the expression of the quantitative character in the population.

The likelihood of identifying a transgressive segregant is greatly reduced as the number of traits combined into one genotype is increased. For example, if a cross is made between cultivars differing in three complex characters, such as yield, α'-subunit content and at least a first agronomic trait, it is extremely difficult without molecular tools to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to a selected gene.

Backcrossing is an efficient method for transferring specific desirable traits. This can be accomplished, for example, by first crossing a superior variety inbred (A) (recurrent parent) to a donor inbred (non-recurrent parent), which carries the appropriate gene(s) for the trait in question (Fehr, 1987). The progeny of this cross are then mated back to the superior recurrent parent (A) followed by selection in the resultant progeny for the desired trait to be transferred from the non-recurrent parent. Such selection can be based on genetic assays or on the phenotype of the progeny plant. After five or more backcross generations with selection for the desired trait, the progeny are heterozygous for loci controlling the characteristic being transferred, but are like the superior parent for most or almost all other genes. The last generation of the backcross is selfed, or sibbed, to give pure breeding progeny for the gene(s) being transferred, for example, loci providing the plant with decreased seed glycinin content.

In one embodiment of the invention, the process of backcross conversion may be defined as a process including the steps of:

(a) crossing a plant of a first genotype containing one or more desirable traits, e.g. increased α'-subunit content in seed, to a plant of a second genotype lacking said desirable trait;

(b) selecting one or more progeny plant(s) containing the desirable trait (c) crossing the progeny plant to a plant of the second genotype; and (d) repeating steps (b) and (c) for the purpose of transferring said desirable trait from a plant of a first genotype to a plant of a second genotype.

Introgression of a particular trait into a plant genotype is defined as the result of the process of backcross conversion. A plant genotype into which a trait has been introgressed may be referred to as a backcross converted genotype, line, inbred, or hybrid. Similarly a plant genotype lacking the desired trait may be referred to as an unconverted genotype, line, inbred, or hybrid. Backcrossing can be used with the present invention to introduce the α'-subunit content trait in accordance with the current invention into any variety by conversion of that trait.

The selection of a suitable recurrent parent is an important step for a successful backcrossing procedure. The goal of a backcross protocol is to alter or substitute a trait or characteristic in the original inbred. To accomplish this, one or more loci of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, which in the case of the present invention may be to add one or more allele(s) conferring increased α'-subunit content. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred. In the case of the present invention, one may test. the α'-subunit content of progeny lines generated during the backcrossing program, for example by SDS-PAGE/Coomassie staining (sodium dodecyl sulfate polyacrylamide gel electrophoresis), Western Blot, capillary electrophoresis (CE), or ELISA (Enzyme-linked ImmunoSorbent Assay)

SDS-PAGE is used to separate proteins according to their electrophoretic mobility (a function of length of polypeptide chain or molecular weight as well as higher order protein folding, posttranslational modifications and other factors). The SDS gel electrophoresis of samples having identical charge to mass ratios results in fractionation by size. Proteins can be identified based on their size. The western blot is a method of detecting specific proteins using gel electrophoresis to separate native or denatured proteins by the length of the polypeptide (denaturing conditions) or by the 3-D structure of the protein (native/non-denaturing conditions). The proteins are then transferred to a membrane, where they are detected using antibodies specific to the target protein. CE is used to separate ionic species by their charge and frictional forces. Proteins are separated based on their size to charge ratio in the interior of a small capillary filled with an electrolyte. CE offers excellent resolution and selectivity allowing for separation of analytes with very little physical difference. ELISA is a biochemical technique used to detect the presence of an antibody or an antigen in a sample. In ELISA an unknown amount of antigen is affixed to a surface, and then a specific antibody is washed over the surface so that it can bind to the antigen, the molecule of interest. This antibody is linked to an enzyme, and in the final step a substance is added that the enzyme can convert to some detectable signal. Thus in the case of fluorescence ELISA, when light is shone upon the sample, any antigen/antibody complexes will fluoresce so that the amount of antigen in the sample can be measured.

Soybean plants (*Glycine max* L.) can be crossed by either natural or mechanical techniques (see, e.g., Fehr, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, 1969; Criswell and Hume, 1972). The critical day length for flowering ranges from about 13 h for genotypes adapted to tropical latitudes to 24 h for photoperiod-insensitive genotypes grown at higher latitudes (Shibles et al., 1975). Soybeans seem to be insensitive to day length for 9 days after emergence. Photoperiods shorter than the critical day length are required for 7 to 26 days to complete flower induction (Borthwick and Parker, 1938; Shanmugasundaram and Tsou, 1978).

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs (Brim and Stuber, 1973). The distance required for complete isolation of a crossing block is not clear; however, outcrossing is less than 0.5% when male-sterile plants are 12 m or more from a foreign pollen source (Boerma and Moradshahi, 1975). Plants on the boundaries of a crossing block probably sustain the most outcrossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

III. Traits for Modification and Improvement of Soybean Varieties

In certain embodiments, a soybean plant provided by the invention may comprise one or more transgene(s). One example of such a transgene confers herbicide resistance. Common herbicide resistance genes include an EPSPS gene conferring glyphosate resistance, a neomycin phosphotransferase II (nptII) gene conferring resistance to kanamycin (Fraley et al, 1983), a hygromycin phosphotransferase gene conferring resistance to the antibiotic hygromycin (Vanden Elzen et al., 1985), genes conferring resistance to glufosinate or broxynil (Comai et al., 1985; Gordon-Kamm et al., 1990; Stalker et al., 1988) such as dihydrofolate reductase and acetolactate synthase (Eichholtz et al., 1987, Shah et al., 1986, Charest et al., 1990). Further examples include mutant ALS and AHAS enzymes conferring resistance to imidazalinone or a sulfonylurea (Lee et al., 1988; Miki et al., 1990), a phosphinothricin-acetyl-transferase gene conferring phosphinothricin resistance (European Appln. 0 242 246), genes conferring resistance to phenoxy proprionic acids and cycloshexones, such as sethoxydim and haloxyfop (Marshall et al., 1992); and genes conferring resistance to triazine (psbA and gs+genes) and benzonitrile (nitrilase gene) (Przibila et al., 1991).

A plant of the invention may also comprise a gene that confers resistance to insect, pest, viral or bacterial attack. For example, a gene conferring resistance to a pest, such as soybean cyst nematode was described in PCT Application WO96/30517 and PCT Application WO93/19181. Jones et al., (1994) describe cloning of the tomato Cf-9 gene for resistance to *Cladosporium fulvum*); Martin et al., (1993) describe a tomato Pto gene for resistance to *Pseudononas syringae* pv. and Mindrinos et al., (1994) describe an *Arabidopsis* RSP2 gene for resistance to *Pseudomonas syringae*, *Bacillus thuringiensis* endotoxins may also be used for insect resistance. (See, for example, Geiser et al. (1986). A vitamin-binding protein such as avidin may also be used as a larvicide (PCT application US93/06487).

The use of viral coat proteins in transformed plant cells is known to impart resistance to viral infection and/or disease development affected by the virus from which the coat protein gene is derived, as well as by related viruses. (See Beachy et al., 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id. Developmental-arrestive proteins produced in nature by a pathogen or a parasite may also be used. For example, Logemann et al., (1992), have shown that transgenic plants expressing the barley ribosome-inactivating gene have an increased resistance to fungal disease.

Transgenes may also be used conferring increased nutritional value or another value-added trait. One example is modified fatty acid metabolism, for example, by transforming a plant with an antisense gene of stearoyl-ACP desaturase to increase stearic acid content of the plant. (See Knutzon et al., 1992). A sense desaturase gene may also be introduced to alter fatty acid content. Phytate content may be modified by introduction of a phytase-encoding gene to enhance breakdown of phytate, adding more free phosphate to the transformed plant. Modified carbohydrate composition may also be affected, for example, by transforming plants with a gene coding for an enzyme that alters the branching pattern of starch. (See Shiroza et al., 1988) (nucleotide sequence of *Streptococcus mutans* fructosyltransferase gene); Steinmetz et al., (1985) (nucleotide sequence of *Bacillus subtilis* levansucrase gene); Pen et al., (1992) (production of transgenic plants that express *Bacillus licheniformis* α-amylase); Elliot et al., (1993) (nucleotide sequences of tomato invertase genes); Søgaard et al., (1993) (site-directed mutagenesis of barley α-amylase gene); and Fisher et al., (1993) (maize endosperm starch branching enzyme II)).

Transgenes may also be used to alter protein metabolism. For example, U.S. Pat. No. 5,545,545 describes lysine-insensitive maize dihydrodipicolinic acid synthase (DHPS), which is substantially resistant to concentrations of L-lysine which otherwise inhibit the activity of native DHPS. Similarly, EP 0640141 describes sequences encoding lysine-insensitive aspartokinase (AK) capable of causing a higher than normal production of theonine, as well as a subfragment encoding antisense lysine ketoglutarate reductase for increasing lysine.

In another embodiment, a transgene may be employed that alters plant carbohydrate metabolism. For example, fructokinase genes are known for use in metabolic engineering of fructokinase gene expression in transgenic plants and their fruit (see U.S. Pat. No. 6,031,154). A further example of transgenes that may be used are genes that alter grain yield. For example, U.S. Pat. No. 6,486,383 describes modification of starch content in plants with subunit proteins of adenosine diphosphoglucose pyrophosphorylase ("ADPG PPase"). In EP0797673, transgenic plants are discussed in which the introduction and expression of particular DNA molecules results in the formation of easily mobilized phosphate pools outside the vacuole and an enhanced biomass production and/or altered flowering behavior. Still further known are genes for altering plant maturity. U.S. Pat. No. 6,774,284 describes DNA encoding a plant lipase and methods of use thereof for controlling senescence in plants. U.S. Pat. No. 6,140,085 discusses FCA genes for altering flowering characteristics, particularly timing of flowering. U.S. Pat. No. 5,637,785 discusses genetically modified plants having modulated flower development such as having early floral meristem development and comprising a structural gene encoding the LEAFY .protein in its genome.

Genes for altering plant morphological characteristics are also known and may be used in accordance with the invention. U.S. Pat. No. 6,184,440 discusses genetically engineered plants which display altered structure or morphology as a result of expressing a cell wall modulation transgene. Examples of cell wall modulation transgenes include a cellulose binding domain, a cellulose binding piotein, or a cell wall modifying protein or enzyme such as endoxyloglucan transferase, xyloglucan endo-transglycosylase, an expansin, cellulose synthase, or a novel isolated endo-1,4-β-glucanase.

Methods for introduction of a transgene are well known in the art and include biological and physical, plant transformation protocols. See, for example, Miki et al. (1993).

Once a transgene is introduced into a variety it may readily be transferred by crossing. By using backcrossing, essentially all of the desired morphological and physiological characteristics of a variety are recovered in addition to the locus transferred into the variety via the backcrossing technique. Backcrossing methods can be used with the present invention to improve or introduce a characteristic into a plant (Poehlman et al., 1995; Fehr, 1987a,b).

IV. Tissue Cultures and In Vitro Regeneration of Soybean Plants

A further aspect of the invention relates to tissue cultures of a soybean variety of the invention. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In a preferred embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. Nos. 4,992,375; 5,015,580; 5,024,944, and 5,416,011, each of the disclosures of which is specifically incorporated herein by reference in its entirety.

An important ability of tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes; shoot morphogenesis and somatic embryogenesis (Finer, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not give rise to germ-line tissue. Once the system is well understood and reproduced satisfactorily, it can be used as one target tissue for soybean transformation.

Somatic embryogenesis in soybean was first reported by Christianson et al. (1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck a al., 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

V. Utilization of Soybean Plants

A soybean plant provided by the invention may be used for any purpose deemed of value. Common uses include the preparation of food for human consumption, feed for non-human animal consumption and industrial uses. As used herein, "industrial use" or "industrial usage" refers to non-food and non-feed uses for soybeans or soy-based products.

Soybeans are commonly processed into two primary products, soybean protein (meal) and crude soybean oil. Both of these products are commonly further refined for particular uses. Refined oil products can be broken down into glycerol, fatty acids and sterols. These can be for food, feed or industrial usage. Edible food product use examples include coffee creamers, margarine, mayonnaise, pharmaceuticals, salad dressings, shortenings, bakery products, and chocolate coatings.

Soy protein products (e.g., meal), can be divided into soy flour concentrates and isolates which have both food/feed and industrial use. Soy flour and grits are often used in the manufacturing of meat extenders and analogs, pet foods, baking ingredients and other food products. Food products made from soy flour and isolate include baby food, candy products, cereals, food drinks, noodles, yeast, beer, ale, etc. Soybean meal in particular is commonly used as a source of protein in livestock feeding, primarily swine and poultry. Feed uses thus include, but are not limited to, aquaculture feeds, bee feeds, calf feed replacers, fish feed, livestock feeds, poultry feeds and pet feeds, etc.

Whole soybean products can also be used as food or feed. Common food usage includes products such as the seed, bean sprouts, baked soybean, full fat soy flour used in various products of baking, roasted soybean used as confectioneries, soy nut butter, soy coffee, and other soy derivatives of oriental foods. For feed usage, hulls are commonly removed from the soybean and used as feed.

Soybeans additionally have many industrial uses. One common industrial usage for soybeans is the preparation of binders that can be used to manufacture composites. For example, wood composites may be produced using modified soy protein, a mixture of hydrolyzed soy protein and PF resins, soy flour containing powder resins, and soy protein containing foamed glues. Soy-based binders have been used to manufacture common wood products such as plywood for over 70 years. Although the introduction of urea-formaldehyde and phenol-formaldehyde resins has decreased the usage of soy-based adhesives in wood products, environmental concerns and consumer preferences for adhesives made from a renewable feedstock have caused a resurgence of interest in developing new soy-based products for the wood composite industry.

Preparation of adhesives represents another common industrial usage for soybeans. Examples of soy adhesives include soy hydrolyzate adhesives and soy flour adhesives. Soy hydrolyzate is a colorless, aqueous solution made by reacting soy protein isolate in a 5 percent sodium hydroxide solution under heat (120° C.) and pressure (30 psig). The resulting degraded soy protein solution is basic (pH 11) and flowable (approximately 500 cps) at room temperature. Soy flour is a finely ground, defatted meal made from soybeans. Various adhesive formulations can be made from soy flour, with the first step commonly requiring dissolving the flour in a sodium hydroxide solution. The strength and other properties of the resulting formulation will vary depending on the additives in the formulation. Soy flour adhesives may also potentially be combined with other commercially available resins.

Soybean oil may find application in a number of industrial uses. Soybean oil is the most readily available and one of the lowest-cost vegetable oils in the world. Common industrial uses for soybean oil include use as components of anti-static agents, caulking compounds, disinfectants, fungicides, inks, paints, protective coatings, wallboard, anti-foam agents, alcohol, margarine, paint, ink, rubber, shortening, cosmetics, etc. Soybean oils have also for many years been a major ingredient in alkyd resins, which are dissolved in carrier solvents to make oil-based paints. The basic chemistry for converting vegetable oils into an alkyd resin under heat and pressure is well understood to those of skill in the art.

Soybean oil in its commercially available unrefined or refined, edible-grade state, is a fairly stable and slow-drying oil. Soybean oil can also be modified to enhance its reactivity under ambient conditions or, with the input of energy in various forms, to cause the oil to copolymerize or cure to a dry film. Some of these forms of modification have included epoxidation, alcoholysis or tranesterification, direct esterification, metathesis, isomerization, monomer modification, and various forms of polymerization, including heat bodying. The reactive linoleic-acid component of soybean oil with its double bonds may be more useful than the predominant oleic- and linoleic-acid components for many industrial uses.

Solvents can also be prepared using soy-based ingredients. For example, methyl soyate, a soybean-oil based methyl ester, is gaining market acceptance as an excellent solvent replacement alternative in applications such as parts cleaning and degreasing, paint and ink removal, and oil spill remediation. It is also being marketed in numerous formulated consumer products including hand cleaners, car waxes and graffiti removers. Methyl soyate is produced by the transesterification of soybean oil with methanol. It is commercially available from numerous manufacturers and suppliers. As a solvent, methyl soyate has important environmental- and safety-related properties that make it attractive for industrial applications. It is lower in toxicity than most other solvents, is readily biodegradable, and has a very high flash point and a low level of volatile organic compounds (VOCs). The compatibility of methyl soyate is excellent with metals, plastics, most elastomers and other organic solvents, Current uses of methyl soyate include cleaners, paint strippers, oil spill cleanup and bioremediation, pesticide adjuvants, corrosion preventives and biodiesel fuels additives.

VI. Definitions

In the description and tables which follow, a number of terms are used. In order to provide a clear and consistent understanding of the specification and claims, the following definitions are provided:

α-subunit: As used herein, means the β-conglycinin α-subunit.

α'-subunit: As used herein, means the β-conglycinin α'-subunit.

β-subunit: As used herein, means the β-conglycinin β-subunit.

A: When used in conjunction with the word "comprising" or other open language in the claims, the words "a" and "an" denote "one or more."

Agronomically Elite: As used herein, means a genotype that has a culmination of many distinguishable traits such as seed yield, emergence, vigor, vegetative vigor, disease resistance, seed set, standability and threshability which allows a producer to harvest a product of commercial significance.

Allele: Any of one or more alternative forms of a gene locus, all of which alleles relate to a trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Commercially Significant Yield: A yield of grain having commercial significance to the grower represented by an actual grain yield of at least 95% of the check lines AG2703 and DKB23-51 when grown under the same conditions.

Crossing: The mating of two parent plants.

Cross-pollination: Fertilization by the union of two gametes from different plants.

Down-regulatory mutation: For the purposes of this application a down regulatory mutation is defined as a mutation that reduces the expression levels of a protein from a given gene. Thus a down-regulatory mutation comprises null mutations.

$F_1$ Hybrid: The first generation progeny of the cross of two nonisogenic plants.

Genotype: The genetic constitution of a cell or organism.

Glycinin null: Mutant soybean plants with mutations conferring reduced glycinin content and increased β-conglycinin content. Plants with increased β-conglycinin contents may have non-transgenic null alleles for Gy1, Gy2, Gy3, Gy4 and/or Gy5.

INDEL: Genetic mutations resulting from insertion or deletion of nucleotide sequence.

Industrial use: A non-food and non-feed use for a soybean plant. The term "soybean plant" includes plant parts and derivatives of a soybean plant.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring, or induced by conventional methods (e.g. exposure of plants to radiation or mutagenic compounds), not including mutations made using recombinant DNA techniques.

Null phenotype: A null phenotype as used herein means that a given protein is not expressed at levels that can be detected. In the case of the Gy subunits, expression levels are determined by SDS-PAGE and Coomassie staining.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

SNP: Refers to single nucleotide polymorphisms, or single nucleotide mutations when comparing two homologous sequences.

Stringent Conditions: Refers to nucleic acid hybridization conditions of 5×SSC, 50% formamide and 42° C.

Substantially Equivalent: A characteristic that, when compared, does not show a statistically significant difference (e.g., $p = 0.05$) from the mean.

Tissue Culture: A composition comprising isolated cells of the same or a different type or a collection of such cells organized into parts of a plant.

Transgene: A genetic locus comprising a sequence which has been introduced into the genome of a soybean plant by transformation.

Nutraceutical: Foods that have a medicinal effect on human health.

Embodiments discussed in the context of a method and/or composition of the invention may be employed with respect to any other method or composition described herein. Thus, an embodiment pertaining to one method or composition may be applied to other methods and compositions of the invention as well.

As used in the specification or claims, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Soybean Varieties with Increased α'-subunit Content

The relative percentages of α', α, and β subunits in the β-conglycinin trimer are ~35, 45, and 20%, respectively (Maruyama et al., 1999). The ratio of α:α' is approximately 1.28 in most seeds. Commercial varieties were screened for increased α'-subunit content. Protein analysis was carried out as follows: soybean seeds from a single variety were pooled and ground using the CAT Mega-Grinder (SOP Asci-01-0002). Ground samples were stored at 4° C. For analysis, ~30 mg of flour from each was weighed into one well of a 96 well 2 ml microtiter plate. Protein was extracted for 1 hour with shaking in 1.0 ml 1× Laemmli SDS buffer pH 6.8 containing 0.1M dithiothreitol (DTT) as a reductant. Following centrifugation, a portion of each extract was further diluted in SDS buffer to yield 0.2-0.5 µg/µL total protein, heated to 90-100° C. for 10 min, and cooled. For each sample, 1-2 µg total protein was loaded using a 12 channel pipet onto a 26 lane 15% T gradient Tris/HCl Criterion gel. Molecular weight standards and a parental control were included in two of the lanes in each gel. The gels were electrophoresed until the tracking dye reached the bottom of the gel ~1.2 hrs, then stained overnight in Colloidal Coomassie Blue G-250, destained in DI water, and imaged using the GS800 Calibrated Densitometer. Quantitation was performed using Bio-Rad Quantity One™ Software. The software was used to determine the relative quantity of each band in the sample lane. The percent acidic glycinin and percent β-conglycinin protein subunit bands are reported as the relative percent of the total protein in the lane. The sample identities and weights are tracked using Master LIMS™.

Results of the screening are presented in Table 1. Notably, the ratio of α:α' was approximately 1.28 in most seeds screened. Varieties with unique seed composition, i.e. wherein the ratio of α:α' was less than 1, were identified and selected for further breeding efforts. Unexpectedly, in the selected varieties, the β-subunit content remained unchanged or conserved despite of the increase in α'-subunit content.

TABLE 1

Protein Content of Select Soybean Varieties

| | PI88788 in lineage | α:α' | Relative Percent of Protein | | | | | | | | | | |
|---|---|---|---|---|---|---|---|---|---|---|---|---|---|
| Variety | | | α' βC | α βC | ββC | Total βC | α1,2,4 Gly | a3 gly | Basic Gly | Total Gly | LOX 2&3 | LOX 1 | KTI |
| MV0053 | N | 1.3 | 8.9 | 11.3 | 6.0 | 26.2 | 15.6 | 3.0 | 14.9 | 29.5 | 5.4 | 1.8 | 2.5 |
| MV0054 | N | 1.3 | 9.6 | 11.5 | 6.6 | 27.8 | 16.3 | 3.5 | 15.1 | 31.4 | 5.6 | 1.9 | 3.0 |
| MV0055 | N | 1.3 | 8.8 | 11.2 | 4.8 | 24.8 | 15.5 | 3.1 | 16.0 | 29.6 | 5.8 | 2.0 | 3.2 |
| MV0056 | N | 1.3 | 8.5 | 10.6 | 5.3 | 24.5 | 16.0 | 3.6 | 15.1 | 31.0 | 4.9 | 1.8 | 2.4 |
| MV0057 | N | 1.3 | 8.8 | 10.5 | 5.3 | 24.6 | 16.5 | 3.5 | 16.7 | 31.8 | 5.6 | 1.9 | 3.2 |
| MV0058 | N | 1.3 | 9.1 | 11.4 | 6.4 | 26.9 | 15.1 | 3.1 | 15.2 | 28.9 | 5.3 | 1.9 | 3.1 |
| MV0059 | N | 1.4 | 8.7 | 12.5 | 6.0 | 27.3 | 14.2 | 2.7 | 14.7 | 27.0 | 6.6 | 2.2 | 4.1 |
| MV0060 | Y | 0.9 | 10.5 | 9.5 | 7.2 | 27.2 | 15.4 | 3.0 | 16.0 | 29.2 | 6.3 | 2.2 | 4.4 |
| MV0030 | N | 1.3 | 8.3 | 10.4 | 4.7 | 23.4 | 15.8 | 3.5 | 16.4 | 30.7 | 5.4 | 1.8 | 3.2 |
| MV0061 | Y | 0.7 | 10.7 | 7.3 | 5.9 | 23.9 | 16.5 | 3.4 | 15.5 | 31.5 | 6.2 | 2.5 | 3.2 |
| MV0062 | Y | 0.8 | 9.7 | 7.6 | 7.7 | 24.9 | 16.0 | 3.8 | 17.9 | 31.5 | 6.0 | 2.4 | 3.7 |
| MV0063 | Y | 0.8 | 9.5 | 7.2 | 7.8 | 24.5 | 15.9 | 3.7 | 16.9 | 31.1 | 5.6 | 2.3 | 3.9 |
| MV0064 | Y | 1.3 | 9.4 | 11.2 | 5.8 | 26.4 | 16.6 | 3.1 | 16.4 | 31.4 | 4.8 | 1.9 | 3.1 |
| MV0065 | Y | 0.7 | 10.3 | 7.4 | 8.8 | 26.5 | 17.0 | 3.7 | 16.8 | 32.8 | 5.4 | 1.9 | 2.5 |
| MV0066 | Y | 0.9 | 8.5 | 7.5 | 7.6 | 23.6 | 17.1 | 3.6 | 18.3 | 32.8 | 5.4 | 1.9 | 3.2 |
| MV0067 | Y | 1.4 | 9.7 | 13.7 | 6.2 | 29.5 | 15.8 | 3.3 | 145 | 30.4 | 5.3 | 2.0 | 2.5 |
| MV0068 | Y | 1.4 | 9.7 | 13.5 | 5.3 | 28.5 | 16.1 | 3.4 | 14.8 | 31.0 | 5.3 | 1.9 | 2.7 |
| MV0069 | Y | 0.8 | 9.4 | 8.0 | 8.8 | 26.2 | 16.5 | 4.1 | 15.6 | 32.7 | 5.8 | 2.2 | 3.6 |

TABLE 1-continued

Protein Content of Select Soybean Varieties

| | PI88788 in lineage | | Relative Percent of Protein | | | | | | | | | | |
|---|---|---|---|---|---|---|---|---|---|---|---|---|---|
| Variety | | α:α' | α' βC | α βC | ββC | Total βC | α1,2,4 Gly | α3 gly | Basic Gly | Total Gly | LOX 2&3 | LOX 1 | KTI |
| MV0070 | N | 1.4 | 8.9 | 11.9 | 5.3 | 26.2 | 14.2 | 3.5 | 15.9 | 28.2 | 7.1 | 2.9 | 3.5 |
| MV0071 | N | 1.3 | 8.5 | 10.8 | 5.4 | 24.6 | 14.2 | 3.5 | 15.2 | 28.1 | 6.8 | 2.6 | 3.9 |

Example 2

Source of Increased α'-subunit Content in Commercial Varieties

After screening commercial varieties for increased α'-subunit content, variety with a seed α:α' ratio of less than 1 was selected for future breeding efforts. In addition, the lineage of each variety was evaluated. Eighty percent of the screened varieties with PI88788 in their background had a α:α' ratio less than 1 (Table 1). Additionally, 100% of the screened varieties with a α:α' ratio less than 1 had PI88788 in their background. Hence, breeders can pre-select varieties for increased α'-subunit by evaluating the pedigree of varieties for PI88788. Protein analysis is needed to verify phenotype, but the pre-selection could reduce the number of plants in an initial screening effort.

Example 3

Combiniation of Glycinin-null and Increased α'-subunit Trait Further Increases α'-subunit Content in Seed Glycinin genes have a direct impact on β-conglycinin content in soybean seeds. Soybean plants with mutations conferring reduced Gy1, Gy2, Gy3, Gy4 and Gy5 protein content have increased β-conglycinin and subsequently increased α'-subunit content in seed. For example, typical soybeans contain around 40% glycinin, 20% β-conglycinin, with the α'-subunit accounting for 9% of total protein. However, increased β-conglycinin soybeans contain, for example, less than 40%, 30%, 20%, or 6% glycinin, and greater than 20%, 30% or 40% β-conglycinin. The mutant soybean plants with mutations conferring reduced glycinin content and increased β-conglycinin content are referred to as glycinin nulls.

Crosses were generated between glycinin null plants derived from B2G2 and plants identified with increased α'-subunit trait. The progeny was screened for protein content including relative percentage of α-, α'-, and β-subunits (Table 2). The α'-subunit content was up to 25.9% total protein. In addition, a plant with both the increased α'-subunit and glycinin null traits produces almost three times more α'-subunit in the seed than a common commercial variety (FIG. 1).

TABLE 2

α-, α'-, and β- subunits seed content in progeny resulting from crosses between plants with reduced glycinin phenotype and plants with increased α'-subunit phenotype.

| Parents | | | Relative Percent Protein | | | | |
|---|---|---|---|---|---|---|---|
| Female | Male | Progeny | α:α' | α' βC | α βC | β- βC | Total βC |
| MV0105/MV0106 | MV0103(B2G2/MV0104) | MV0072:0002. | 1.4 | 15.6 | 21.5 | 8.0 | 45.1 |
| MV0105/MV0106 | MV0103(B2G2/MV0104) | MV0072:0004. | 1.4 | 14.2 | 19.3 | 7.3 | 40.8 |
| MV0105/MV0106 | MV0103(B2G2/MV0104) | MV0072:0009. | 1.4 | 15.6 | 21.0 | 9.8 | 46.4 |
| MV0105/MV0106 | MV0103(B2G2/MV0104) | MV0072:0010. | 1.4 | 16.4 | 21.9 | 8.9 | 47.2 |
| MV0105/MV0106 | MV0103(B2G2/MV0104) | MV0072:0011. | 1.4 | 16.7 | 22.4 | 8.7 | 47.7 |
| MV0105/MV0106 | MV0103(B2G2/MV0104) | MV0072:0012. | 1.3 | 16.8 | 22.3 | 7.4 | 46.5 |
| MV0105/MV0106 | MV0103(B2G2/MV0104) | MV0072:0013. | 1.3 | 18.2 | 24.0 | 11.5 | 53.7 |
| MV0105/MV0106 | MV0103(B2G2/MV0104) | MV0072:0016. | 1.3 | 18.5 | 24.4 | 7.4 | 50.3 |
| MV0105/MV0106 | MV0103(B2G2/MV0104) | MV0072:0017. | 1.3 | 16.8 | 22.0 | 7.7 | 46.5 |
| MV0105/MV0106 | MV0103(B2G2/MV0104) | MV0072:0018. | 1.3 | 15.7 | 20.3 | 7.6 | 43.6 |
| MV0105/MV0106 | MV0103(B2G2/MV0104) | MV0072:0019. | 1.3 | 14.8 | 19.1 | 4.1 | 38.0 |
| MV0105/MV0106 | MV0103(B2G2/MV0104) | MV0072:0022. | 1.3 | 16.2 | 20.8 | 6.4 | 43.5 |
| MV0105/MV0106 | MV0103(B2G2/MV0104) | MV0072:0023. | 1.3 | 15.7 | 20.0 | 7.9 | 43.5 |
| MV0105/MV0106 | MV0103(B2G2/MV0104) | MV0072:0024. | 1.3 | 14.0 | 17.7 | 6.1 | 37.7 |
| MV0105/MV0106 | MV0103(B2G2/MV0104) | MV0072:0027. | 1.3 | 14.7 | 18.7 | 8.0 | 41.4 |
| MV0105/MV0106 | MV0103(B2G2/MV0104) | MV0072:0028. | 1.3 | 14.9 | 18.8 | 9.3 | 43.1 |
| MV0105/MV0106 | MV0103(B2G2/MV0104) | MV0072:0033. | 1.3 | 15.9 | 20.0 | 9.2 | 45.0 |
| MV0105/MV0106 | MV0103(B2G2/MV0104) | MV0072:0034. | 1.3 | 15.5 | 19.3 | 4.2 | 39.0 |
| MV0105/MV0106 | MV0103(B2G2/MV0104) | MV0072:0035. | 1.3 | 16.8 | 21.1 | 7.5 | 45.4 |
| MV0105/MV0106 | MV0103(B2G2/MV0104) | MV0072:0037. | 1.3 | 16.4 | 20.4 | 9.3 | 46.2 |
| MV0105/MV0106 | MV0103(B2G2/MV0104) | MV0072:0039. | 1.3 | 17.0 | 13.6 | 17.0 | 8.8 39.4 |
| MV0105/MV0106 | MV0103(B2G2/MV0104) | MV0072:0041. | 1.3 | 13.5 | 16.9 | 8.1 | 38.6 |
| MV0105/MV0106 | MV0103(B2G2/MV0104) | MV0072:0047. | 1.3 | 14.0 | 17.4 | 5.7 | 37.1 |
| MV0105/MV0106 | MV0103(B2G2/MV0104) | MV0072:0049. | 1.3 | 15.5 | 19.3 | 9.8 | 44.6 |
| MV0061 | MV0103(B2G2/MV0104) | MV0073:0001. | 1.0 | 19.0 | 18.5 | 7.5 | 45.0 |
| MV0061 | MV0103(B2G2/MV0104) | MV0073:0002. | 1.0 | 14.4 | 13.9 | 5.2 | 33.4 |

TABLE 2-continued

α-, α'-, and β- subunits seed content in progeny resulting from crosses between plants with reduced glycinin phenotype and plants with increased α'-subunit phenotype.

| Parents | | | | Relative Percent Protein | | | |
|---|---|---|---|---|---|---|---|
| Female | Male | Progeny | α:α' | α' βC | α βC | β- βC | Total βC |
| MV0061 | MV0103(B2G2/MV0104) | MV0073:0003. | 0.9 | 20.6 | 19.1 | 9.6 | 49.3 |
| MV0061 | MV0103(B2G2/MV0104) | MV0073:0004. | 0.9 | 18.9 | 17.0 | 11.8 | 47.7 |
| MV0061 | MV0103(B2G2/MV0104) | MV0073:0005. | 0.9 | 20.4 | 18.1 | 8.5 | 47.0 |
| MV0061 | MV0103(B2G2/MV0104) | MV0073:0006. | 0.9 | 13.0 | 11.3 | 5.0 | 29.3 |
| MV0061 | MV0103(B2G2/MV0104) | MV0073:0007. | 0.8 | 21.0 | 17.9 | 12.2 | 51.1 |
| MV0061 | MV0103(B2G2/MV0104) | MV0073:0008. | 0.8 | 12.0 | 10.1 | 6.7 | 28.8 |
| MV0061 | MV0103(B2G2/MV0104) | MV0073:0009. | 0.8 | 20.1 | 15.5 | 11.3 | 46.9 |
| MV0061 | MV0103(B2G2/MV0104) | MV0073:0010. | 0.7 | 20.4 | 13.8 | 10.9 | 45.1 |
| MV0061 | MV0103(B2G2/MV0104) | MV0073:0011. | 0.7 | 23.2 | 15.6 | 9.1 | 47.9 |
| MV0061 | MV0103(B2G2/MV0104) | MV0073:0012. | 0.7 | 21.7 | 14.5 | 10.2 | 46.4 |
| MV0061 | MV0103(B2G2/MV0104) | MV0073:0013. | 0.7 | 25.3 | 17.0 | 8.0 | 50.3 |
| MV0061 | MV0103(B2G2/MV0104) | MV0073:0014. | 0.7 | 23.3 | 15.6 | 12.2 | 51.1 |
| MV0061 | MV0103(B2G2/MV0104) | MV0073:0015. | 0.7 | 21.6 | 14.2. | 10.7 | 46.5 |
| MV0061 | MV0103(B2G2/MV0104) | MV0073:0016. | 0.7 | 22.6 | 15.0 | 9.9 | 47.5 |
| MV0061 | MV0103(B2G2/MV0104) | MV0073:0017. | 0.7 | 19.8 | 12.8 | 7.5 | 40.2 |
| MV0061 | MV0103(B2G2/MV0104) | MV0073:0018. | 0.7 | 22.0 | 14.3 | 10.3 | 46.6 |
| MV0061 | MV0103(B2G2/MV0104) | MV0073:0019. | 0.7 | 23.5 | 15.3 | 9.3 | 48.1 |
| MV0061 | MV0103(B2G2/MV0104) | MV0073:0020. | 0.7 | 20.0 | 12.9 | 9.5 | 42.4 |
| MV0061 | MV0103(B2G2/MV0104) | MV0073:0021. | 0.7 | 23.3 | 15.0 | 10.3 | 48.7 |
| MV0061 | MV0103(B2G2/MV0104) | MV0073:0022. | 0.7 | 25.5 | 16.5 | 11.3 | 53.3 |
| MV0061 | MV0103(B2G2/MV0104) | MV0073:0023. | 0.7 | 24.5 | 16.0 | 9.8 | 50.2 |
| MV0061 | MV0103(B2G21MV0104) | MV0073:0024. | 0.6 | 20.1 | 12.9 | 11.3 | 44.3 |
| MV0061 | MV0103(B2G2/MV0104) | MV0073:0025. | 0.6 | 18.1 | 11.6 | 10.0 | 39.7 |
| MV0061 | MV0103(B2G2/MV0104) | MV0073:0026. | 0.6 | 23.5 | 15.1 | 85 | 47.0 |
| MV0061 | MV0103(B2G2/MV0104) | MV0073:0028. | 0.6 | 18.5 | 11.8 | 9.6 | 39.9 |
| MV0061 | MV0103(B2G2/MV0104) | MV0073:0029. | 0.6 | 23.2 | 14.7 | 10.9 | 48.8 |
| MV0061 | MV0103(B2G2/MV0104) | MV0073:0031. | 0.6 | 22.2 | 14.3 | 10.4 | 46.8 |
| MV0061 | MV0103(B2G2/MV0104) | MV0073:0032. | 0.6 | 19.3 | 12.2 | 10.2 | 41.7 |
| MV0061 | MV0103(B2G2/MV0104) | MV0073:0033. | 0.6 | 20.8 | 13.2 | 11.7 | 45.7 |
| MV0061 | MV0103(B2G2/MV0104) | MV0073:0034. | 0.6 | 18.7 | 11.8 | 8.6 | 39.1 |
| MV0061 | MV0103(B2G2/MV0104) | MV0073:0035. | 0.6 | 19.3 | 12.1 | 10.3 | 41.8 |
| MV0061 | MV0103(B2G2/MV0104) | MV0073:0036. | 0.6 | 20.6 | 13.0 | 9.6 | 43.2 |
| MV0061 | MV0103(B2G2/MV0104) | MV0073:0037. | 0.6 | 23.5 | 14.8 | 9.9 | 48.2 |
| MV0061 | MV0103(B2G2/MV0104) | MV0073:0038. | 0.6 | 24.4 | 15.3 | 8.0 | 47.7 |
| MV0061 | MV0103(B2G2/MV0104) | MV0073:0039. | 0.6 | 25.5 | 16.0 | 10.0 | 51.6 |
| MV0061 | MV0103(B2G2/MV0104) | MV0073:0040. | 0.6 | 17.9 | 11.4 | 10.5 | 39.8 |
| MV0107 | MV0103(B2G2/MV0104) | MV0074:0001. | 1.1 | 12.8 | 14.3 | 7.4 | 34.5 |
| MV0107 | MV0103(B2G2/MV0104) | MV0074:0002. | 1.1 | 18.2 | 20.5 | 7.4 | 46.2 |
| MV0107 | MV0103(B2G2/MV0104) | MV0074:0003. | 1.1 | 12.4 | 14.0 | 7.7 | 34.1 |
| MV0107 | MV0103(B2G2/MV0104) | MV0074:0004. | 1.1 | 17.1 | 19.2 | 10.5 | 46.8 |
| MV0107 | MV0103(B2G2/MV0104) | MV0074:0005. | 1.1 | 16.3 | 18.3 | 9.8 | 44.4 |
| MV0107 | MV0103(B2G2/MV0104) | MV0074:0010. | 1.1 | 15.7 | 17.6 | 9.2 | 42.5 |
| MV0107 | MV0103(B2G2/MV0104) | MV0074:0011. | 1.1 | 13.4 | 15.0 | 7.7 | 36.1 |
| MV0107 | MV0103(B2G2/MV0104) | MV0074:0012. | 1.1 | 16.2 | 18.0 | 6.8 | 41.0 |
| MV0107 | MV0103(B2G2/MV0104) | MV0074:0013. | 1.1 | 13.5 | 15.0 | 8.4 | 36.8 |
| MV0107 | MV0103(B2G2/MV0104) | MV0074:0014. | 1.1 | 16.1 | 17.9 | 8.8 | 42.8 |
| MV0107 | MV0103(B2G2/MV0104) | MV0074:0019. | 1.1 | 15.1 | 16.6 | 4.2 | 35.8 |
| MV0107 | MV0103(B2G2/MV0104) | MV0074:0020. | 1.1 | 16.6 | 18.3 | 5.3 | 40.3 |
| MV0107 | MV0103(B2G2/MV0104) | MV0074:0021. | 1.1 | 11.6 | 12.8 | 4.9 | 29.3 |
| MV0107 | MV0103(B2G2/MV0104) | MV0074: 0022. | 1.1 | 13.1 | 14.5 | 9.5 | 37.1 |
| MV0107 | MV0103(B2G2/MV0104) | MV0074:0023. | 1.1 | 15.6 | 17.2 | 7.9 | 40.7 |
| MV0107 | MV0103(B2G2/MV0104) | MV0074:0024. | 1.1 | 14.2 | 15.5 | 6.6 | 36.3 |
| MV0107 | MV0103(B2G2/MV0104) | MV0074:0025. | 1.1 | 17.6 | 19.1 | 7.3 | 43.9 |
| MV0107 | MV0103(B2G2/MV0104) | MV0074:0027. | 1.1 | 15.8 | 17.3 | 7.4 | 40.5 |
| MV0107 | MV0103(B2G2/MV0104) | MV0074:0028. | 1.1. | 15.7 | 17.1 | 6.3 | 39.1 |
| MV0107 | MV0103(B2G2/MV0104) | MV0074:0029. | 1.1 | 14.9 | 16.2 | 7.7 | 38.8 |
| MV0107 | MV0103(B2G2/MV0104) | MV0074:0030. | 1.1 | 15.5 | 16.8 | 9.1 | 41.3 |
| MV0107 | MV0103(B2G2/MV0104) | MV0074:0033. | 1.1 | 13.7 | 14.8 | 8.1 | 36.6 |
| MV0107 | MV0103(B2 G2/MV0104) | MV0074:0034. | 1.1 | 12.1 | 13.0 | 5.2 | 30.3 |
| MV0107 | MV0103(B2G2/MV0104) | MV0074:0035. | 1.1 | 15.3 | 16.3 | 3.8 | 35.4 |
| MV0107 | MV0103(B2G2/MV0104) | MV0074:0036. | 1.1 | 17.2 | 18.4 | 7.7 | 43.3 |
| MV0107 | MV0103(B2G2/MV0104) | MV0074:0038. | 1.1 | 13.0 | 13.9 | 6.4 | 33.4 |
| MV0107 | MV0103(B2G2/MV0104) | MV0074:0039. | 1.1 | 12.8 | 13.6 | 4.6 | 30.9 |
| MV0107 | MV0103(B2G2/MV0104) | MV0074:0040. | 1.1 | 18.3 | 19.4 | 4.6 | 42.3 |
| MV0107 | MV0103(B2G2/MV0104) | MV0074:0043. | 1.1 | 17.4 | 18.4 | 8.2 | 44.0 |
| MV0107 | MV0103(B2G2/MV0104) | MV0074: 0044. | 1.0 | 14.6 | 15.4 | 6.6 | 36.7 |
| MV0107 | MV0103(B2G2/MV0104) | MV0074:0046. | 1.0 | 16.6 | 17.2 | 8.0 | 41.7 |
| MV0107 | MV0103(B2G2/MV0104) | MV0074:0047. | 1.0 | 12.6 | 13.1 | 5.9 | 31.6 |
| MV0107 | MV0103(B2G2/MV0104) | MV0074:0048. | 1.0 | 16.5 | 17.0 | 4.7 | 38.2 |
| MV0107 | MV0103(B2G2/MV0104) | MV0074:0049. | 1.0 | 11.3 | 11.7 | 4.4 | 27.5 |
| MV0107 | MV0103(B2G2/MV0104) | MV0074:0050. | 1.0 | 20.3 | 19.8 | 12.2 | 52.3 |
| MV0108 | MV0103(B2G2/MV0104) | MV0075:0001. | 1.1 | 15.7 | 18.2 | 73 | 41.2 |
| MV0108 | MV0103(B2G2/MV0104) | MV0075:0003. | 1.1 | 14.4 | 16.7 | 10.3 | 41.3 |

TABLE 2-continued

α-, α'-, and β- subunits seed content in progeny resulting from crosses between plants with reduced glycinin phenotype and plants with increased α'-subunit phenotype.

| Parents | | | | Relative Percent Protein | | | |
|---|---|---|---|---|---|---|---|
| Female | Male | Progeny | α:α' | α' βC | α βC | β- βC | Total βC |
| MV0108 | MV0103(B2G2/MV0104) | MV0075: 0004. | 1.1 | 16.0 | 18.6 | 7.6 | 42.2 |
| MV0108 | MV0103(B2G2/MV0104) | MV0075: 0005. | 1.1 | 16.0 | 18.5 | 7.9 | 42.3 |
| MV0108 | MV0103(B2G2/MV0104) | MV0075:0006. | 1.1 | 15.4 | 17.8 | 8.4 | 41.6 |
| MV0108 | MV0103(B2G2/MV0104) | MV0075:0008. | 1.1 | 16.8 | 19.4 | 9.0 | 45.3 |
| MV0108 | MV0103(B2G2/MV0104) | MV0075:0009. | 1.1 | 15.1 | 173 | 7.2 | 39.6 |
| MV0108 | MV0103(B2G2/MV0104) | MV0075:0010. | 1.1 | 16.3 | 18.8 | 8.0 | 43.2 |
| MV0108 | MV0103(B2G2/MV0104) | MV0075:0013. | 1.1 | 14.4 | 16.5 | 4.5 | 35.4 |
| MV0108 | MV0103(B2G2/MV0104) | MV0075:0015. | 1.1 | 16.4 | 18.6 | 5.2 | 40.2 |
| MV0108 | MV0103(B2G2/MV0104) | MV0075: 0017. | 1.1 | 16.9 | 19.4 | 6.3 | 42.6 |
| MV0108 | MV0103(B2G2/MV0104) | MV0075:0019. | 1.1 | 12.7 | 14.6 | 7.9 | 35.2 |
| MV0108 | MV0103(B2G2/MV0104) | MV0075:0020. | 1.1 | 15.0 | 17.1 | 8.5 | 40.6 |
| MV0108 | MV0103(B2G2/MV0104) | MV0075:0023. | 1.1 | 14.9 | 17.0 | 8.8 | 40.7 |
| MV0108 | MV0103(B2G2/MV0104) | MV0075:0025. | 1.1 | 14.3 | 16.3 | 7.9 | 38.6 |
| MV0108 | MV0103(B2G2/MV0104) | MV0075:0028. | 1.1 | 12.7 | 14.3 | 6.5 | 33.5 |
| MV0108 | MV0103(B2G2/MV0104) | MV0075:0030. | 1.1 | 13.4 | 15.1 | 4.3 | 32.8 |
| MV0108 | MV0103(B2G2/MV0104) | MV0075:0031. | 1.1 | 15.0 | 17.0 | 6.5 | 38.5 |
| MV0108 | MV0103(B2G2/MV0104) | MV0075:0034. | 1.1 | 13.9 | 15.7 | 7.7 | 37.3 |
| MV0108 | MV0103(B2G2/MV0104) | MV0075:0035. | 1.1 | 14.3 | 16.2 | 9.8 | 40.4 |
| MV0108 | MV0103(B2G2/MV0104) | MV0075:0036. | 1.1 | 13.4 | 15.1 | 7.0 | 35.5 |
| MV0108 | MV0103(B2G2/MV0104) | MV0075:0037. | 1.1 | 17.0 | 19.2 | 7.5 | 43.7 |
| MV0108 | MV0103(B2G2/MV0104) | MV0075:0038. | 1.1 | 13.8 | 15.6 | 8.6 | 38.0 |
| MV0108 | MV0103(B2G2/MV0104) | MV0075:0039. | 1.1 | 14.8 | 16.8 | 7.8 | 39.4 |
| MV0108 | MV0103(B2G2/MV0104) | MV0075:0040. | 1.1 | 17.4 | 19.6 | 6.8 | 43.8 |
| MV0108 | MV0103(B2G2/MV0104) | MV0075:0041. | 1.1 | 15.9 | 17.8 | 4.5 | 38.2 |
| MV0108 | MV0103(B2G2/MV0104) | MV0075:0043. | 1.1 | 14.5 | 16.3 | 4.8 | 35.7 |
| MV0108 | MV0103(B2G2/MV0104) | MV0075:0044. | 1.1 | 14.9 | 16.7 | 7.4 | 39.0 |
| MV0108 | MV0103(B2G2/MV0104) | MV0075:0048. | 1.1 | 14.5 | 16.2 | 7.0 | 37.8 |
| MV0108 | MV0103(B2G2/MV0104) | MV0075: 0050. | 1.1 | 16.3 | 18.2 | 6.0 | 40.5 |
| MV0108 | MV0103(B2G2/MV0104) | MV0076:0021. | 13 | 16.5 | 20.4 | 9.0 | 45.9 |
| MV0108 | MV0103(B2G2/MV0104) | MV0076:0027. | 1.3 | 16.6 | 20.5 | 10.0 | 47.0 |
| MV0108 | MV0103(B2G2/MV0104) | MV0076:0028. | 1.3 | 16.4 | 20.2 | 6.3 | 42.9 |
| MV0108 | MV0103(B2G2/MV0104) | MV0076:0030. | 1.3 | 17.9 | 22.0 | 9.8 | 49.7 |
| MV0108 | MV0103(B2G2/MV0104) | MV0076:0032. | 1.3 | 14.1 | 17.3 | 8.0 | 39.4 |
| MV0108 | MV0103(B2G2/MV0104) | MV0076:0034. | 1.3 | 16.3 | 20.1 | 10.3 | 46.7 |
| MV0108 | MV0103(B2G2/MV0104) | MV0076:0036. | 1.3 | 14.4 | 17.6 | 9.0 | 41.0 |
| MV0108 | MV0103(B2G2/MV0104) | MV0076:0040. | 1.3 | 16.9 | 20.5 | 9.5 | 47.0 |
| MV0108 | MV0103(B2G2/MV0104) | MV0076:0042. | 1.3 | 17.4 | 21.0 | 4.7 | 43.1 |
| MV0108 | MV0103(B2G2/MV0104) | MV0076:0043. | 1.3 | 17.5 | 21.1 | 6.8 | 45.3 |
| MV0108 | MV0103(B2G2/MV0104) | MV0076:0044. | 1.3 | 17.9 | 21.7 | 7.9 | 47.6 |
| MV0108 | MV0103(B2G2/MV0104) | MV0076:0046. | 1.3 | 15.3 | 18.6 | 8.2 | 42.1 |
| MV0108 | MV0103(B2G2/MV0104) | MV0076:0047. | 1.3 | 16.7 | 20.3 | 8.9 | 45.9 |
| MV0108 | MV0103(B2G2/MV0104) | MV0076:0048. | 1.3 | 16.2 | 19.7 | 7.8 | 43.7 |
| MV0108 | MV0103(B2G2/MV0104) | MV0076:0049. | 1.3 | 17.1 | 20.5 | 7.2 | 44.8 |
| MV0107 | MV0103(B2G2/MV0104) | MV0077:0001. | 1.3 | 15.5 | 18.5 | 4.9 | 39.0 |
| MV0107 | MV0103(B2G2/MV0104) | MV0077:0003. | 1.3 | 17.2 | 20.5 | 6.8 | 44.6 |
| MV0107 | MV0103(B2G2/MV0104) | MV0077:0008. | 1.3 | 16.4 | 19.5 | 7.8 | 43.8 |
| MV0107 | MV0103(B2G2/MV0104) | MV0077:0010. | 1.3 | 17.6 | 21.0 | 10.0 | 48.6 |
| MV0107 | MV0103(B2G2/MV0104) | MV0077:0012. | 1.3 | 15.3 | 18.1 | 9.7 | 43.1 |
| MV0107 | MV0103(B2G2/MV0104) | MV0077:0014. | 1.3 | 18.5 | 22.0 | 9.3 | 49.8 |
| MV0107 | MV0103(B2G2/MV0104) | MV0077:0015. | 1.3 | 16.8 | 20.0 | 8.8 | 45.5 |
| MV0107 | MV0103(B2G2/MV0104) | MV0077:0017. | 1.3 | 15.5 | 18.3 | 7.1 | 4.0.8 |
| MV0107 | MV0103(B2G2/MV0104) | MV0077:0020. | 1.3 | 16.5 | 19.6 | 8.2 | 44.3 |
| MV0107 | MV0103(B2G2/MV0104) | MV0077:0022. | 1.3 | 14.4 | 17.0 | 6.2 | 37.6 |
| MV0107 | MV0103(B2G2/MV0104) | MV0077:0023. | 1.3 | 15.1 | 17.8 | 7.5 | 40.3 |
| MV0107 | MV0103(B2G2/MV0104) | MV0077:0024. | 1.3 | 15.1 | 17.9 | 8.8 | 41.7 |
| MV0107 | MV0103(B2G2/MV0104) | MV0077:0025. | 1.1 | 14.8 | 17.2 | 8.6 | 40.6 |
| MV0107 | MV0103(B2G2/MV0104) | MV0077:0026. | 1.1 | 18.8 | 22.1 | 6.7 | 47.6 |
| MV0107 | MV0103(B2G2/MV0104) | MV0077:0028. | 1.1 | 19.0 | 22.3 | 6.9 | 48.3 |
| MV0107 | MV0103(B2G2/MV0104) | MV0077:0030. | 1.1 | 17.0 | 20.0 | 9.3 | 46.4 |
| MV0107 | MV0103(B2G2/MV0104) | MV0077:0031. | 1.1 | 18.9 | 22.2 | 7.3 | 48.3 |
| MV0107 | MV0103(B2G2/MV0104) | MV0077:0035. | 1.1 | 16.1 | 18.9 | 6.7 | 41.7 |
| MV0107 | MV0103(B2G2/MV0104) | MV0077:0036. | 1.1 | 14.2 | 16.7 | 9.2 | 40.1 |
| MV0107 | MV0103(B2G2/MV0104) | MV0077:0037. | 1.1 | 15.4 | 18.0 | 9.2 | 42.6 |
| MV0107 | MV0103(B2G2/MV0104) | MV0077:0038. | 1.1 | 17.8 | 20.9 | 7.6 | 46.3 |
| MV0107 | MV0103(B2G2/MV0104) | MV0077: 0039. | 1.1 | 16.9 | 19.8 | 6.1 | 42.8 |
| MV0107 | MV0103(B2G2/MV0104) | MV0077:0045. | 1.1 | 14.0 | 16.3 | 4.8 | 35.1 |
| MV0107 | MV0103(B2G2/MV0104) | MV0077:0049. | 1.1 | 16.6 | 19.3 | 7.6 | 43.5 |
| MV0107 | MV0103(B2G2/MV0104) | MV0077:0050. | 1.1 | 15.6 | 18.1 | 6.5 | 40.1 |
| MV0061 | MV0103(B2G2/MV0104) | MV0078: 0001. | 0.6 | 26.1 | 16.5 | 10.1 | 52.8 |
| MV0061 | MV0103(B2G2/MV0104) | MV0078:0002. | 0.6 | 24.9 | 15.7 | 9.5 | 50.0 |
| MV0061 | MV0103(B2G2/MV0104) | MV0078:0003. | 0.6 | 22.2 | 14.1 | 6.7 | 43.0 |
| MV0061 | MV0103(B2G2/MV0104) | MV0078:0004. | 0.6 | 24.1 | 15.2 | 10.3 | 49.6 |
| MV0061 | MV0103(B2G2/MV0104) | MV0078:0005. | 0.6 | 21.9 | 13.7 | 11.2 | 46.8 |

TABLE 2-continued

α-, α'-, and β- subunits seed content in progeny resulting from crosses between plants with reduced glycinin phenotype and plants with increased α'-subunit phenotype.

| Parents | | | Relative Percent Protein | | | | |
|---|---|---|---|---|---|---|---|
| Female | Male | Progeny | α:α' | α' βC | α βC | β- βC | Total βC |
| MV0061 | MV0103(B2G2/MV0104) | MV0078:0006. | 0.6 | 22.3 | 14.0 | 9.4 | 45.7 |
| MV0061 | MV0103(B2G2/MV0104) | MV0078: 0007. | 0.6 | 21.6 | 13.6 | 12.7 | 47.9 |
| MV0061 | MV0103(B2G2/MV0104) | MV0078:0008. | 0.6 | 23.7 | 15.0 | 9.7 | 48.4 |
| MV0061 | MV0103(B2G2/MV0104) | MV0078:0009. | 0.6 | 22.8 | 14.4 | 11.4 | 48.6 |
| MV0061 | MV0103(B2G2/MV0104) | MV0078:0010. | 0.6 | 23.7 | 14.6 | 8.9 | 47.2 |
| MV0061 | MV0103(B2G2/MV0104) | MV0078:0011. | 0.6 | 20.6 | 12.8 | 10.5 | 43.9 |
| MV0061 | MV0103(B2G2/MV0104) | MV0078:0012. | 0.6 | 17.0 | 10.6 | 11.0 | 38.7 |
| MV0061 | MV0103(B2G2/MV0104) | MV0078:0014. | 0.6 | 23.6 | 14.5 | 12.2 | 50.3 |
| MV0061 | MV0103(B2G2/MV0104) | MV0078:0016. | 0.6 | 20.1 | 12.5 | 11.2 | 43.7 |
| MV0061 | MV0103(B2G2/MV0104) | MV0078:0017. | 0.6 | 24.9 | 15.5 | 10.1 | 50.5 |
| MV0061 | MV0103(B2G2/MV0104) | MV0078:0018. | 0.6 | 22.6 | 14.1 | 9.6 | 46.2 |
| MV0061 | MV0103(B2G2/MV0104) | MV0078:0019. | 0.6 | 20.8 | 12.9 | 11.0 | 44.7 |
| MV0061 | MV0103(B2G2/MV0104) | MV0078:0020. | 0.6 | 24.0 | 14.9 | 8.6 | 47.5 |
| MV0061 | MV0103(B2G2/MV0104) | MV0078:0021. | 0.6 | 22.1 | 13.8 | 8.9 | 44.8 |
| MV0061 | MV0103(B2G2/MV0104) | MV0078:0022. | 0.6 | 24.7 | 15.2 | 9.9 | 49.8 |
| MV0061 | MV0103(B2G2/MV0104) | MV0078:0024. | 0.6 | 23.1 | 14.4 | 10.4 | 47.9 |
| MV0061 | MV0103(B2G2/MV0104) | MV0078:0025. | 0.6 | 21.8 | 13.4 | 10.7 | 45.9 |
| MV0061 | MV0103(B2G2/MV0104) | MV0078:0026. | 0.6 | 24.8 | 15.2 | 10.1 | 50.1 |
| MV0061 | MV0103(B2G2/MV0104) | MV0078:0027. | 0.6 | 20.8 | 12.7 | 11.4 | 44.9 |
| MV0061 | MV0103(B2G2/MV0104) | MV0078:0028. | 0.6 | 21.2 | 13.0 | 11.1 | 45.3 |
| MV0061 | MV0103(B2G2/MV0104) | MV0078:0029. | 0.6 | 20.8 | 12.4 | 8.9 | 42.0 |
| MV0061 | MV0103(B2G2/MV0104) | MV0078:0030. | 0.6 | 24.3 | 14.5 | 9.7 | 48.5 |
| MV0061 | MV0103(B2G2/MV0104) | MV0078:0031. | 0.6 | 20.5 | 12.4 | 11.0 | 43.9 |
| MV0061 | MV0103(B2G2/MV0104) | MV0078:0032. | 0.6 | 24.8 | 15.0 | 8.8 | 48.6 |
| MV0061 | MV0103(B2G2/MV0104) | MV0078:0033. | 0.6 | 21.1 | 12.6 | 11.1 | 44.7 |
| MV0061 | MV0103(B2G2/MV0104) | MV0078:0034. | 0.6 | 21.0 | 12.6 | 8.4 | 41.9 |
| MV0061 | MV0103(B2G2/MV0104) | MV0078:0035. | 0.6 | 21.8 | 12.9 | 9.4 | 44.1 |
| MV0061 | MV0103(B2G2/MV0104) | MV0078:0036. | 0.6 | 21.8 | 12.9 | 9.2 | 43.9 |
| MV0061 | MV0103(B2G2/MV0104) | MV0078:0038. | 0.6 | 25.9 | 15.3 | 9.3 | 50.6 |
| MV0061 | MV0103(B2G2/MV0104) | MV0078:0039. | 0.6 | 22.8 | 13.5 | 10.0 | 46.3 |
| MV0061 | MV0103(B2G2/MV0104) | MV0078:0040. | 0.6 | 22.2 | 12.6 | 12.0 | 46.8 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,992,375
U.S. Pat. No. 5,015,580
U.S. Pat. No. 5,024,944
U.S. Pat. No. 5,416,011
U.S. Pat. No. 5,545,545
U.S. Pat. No. 5,637,785
U.S. Pat. No. 6,031,154
U.S. Pat. No. 6,140,085
U.S. Pat. No. 6,184,440
U.S. Pat. No. 6,486,383
U.S. Pat. No. 6,774,284
Adams et al., *J. Nutr.*, 134(3):511-516, 2004.
Agui et al. Peptide Science 2005: 195-198, 2005.
Allard, In: *Principles of Plant Breeding*, John Wiley & Sons, N.Y., 50-98, 1960.
Baba et al., *J. Nutr. Sci. Vitaminol. (Tokyo)*, 50(1):26-31, 2004.
Beachy et al., *Ann. rev. Phytopathol.* 28:451, 1990.
Beilinson et al., *Theor. Appl. Genet.*, 104(6-7):1132-1140, 2002.
Boerma and Moradshahi, *Crop Sci.*, 15:858-861, 1975.
Borthwick and Parker, *Bot. Gaz.*, 100:374-387, 1938.
Brim and Stuber, *Crop Sci.*, 13:528-530, 1973.
Charest et al., *Plant Cell Rep.* 8:643 (1990
Chen and Shoemaker, *J. Hered.*, 89:211-215, 1998.
Chrispeels et al., *J. Cell Biol.*, 93:306-313, 1982.
Christianson et al., *Science*, 222:632-634, 1983.
Comai et al., *Nature* 317:741-744 (1985)
Criswell and Hume, *Crop Sci.*, 12:657-660, 1972.
Diers et al., *Theor. Appl. Genet.*, 89:297-304, 1993.
Duranti et al., *J. Nutr.*, 134(6):1334-1339, 2004.
Eichholtz et al., *Somatic Cell Mol. Genet.* 13:67 (1987)
Elliot et al., *Plant Molec. Biol.* 21:515 (1993
European Appln. 0 242 246
European Appln. 0640141
European Appln. 0797673
Fehr, In: *Theory and Technique*, and *Crop Species Soybean*, Iowa State Univ., Macmillian Pub. Co., NY, (1)(2):360-376, 1987b.
Fehr, In: Soybeans: Improvement, Production and Uses, 2nd Edition, Manograph., 16:249, 1987a.

Fehr, In: *Hybridization of Crop Plants*, Fehr and Hadley (Eds.), Am. Soc. Agron. and Crop Sci. Soc. Am., Madison, Wis., 90-599, 1980.

Finer et al., In: *Soybean: Genetics, Molecular Biology and Biotechnology*, CAB Intl., Verma and Shoemaker (ed), Wallingford, Oxon, UK, 250-251, 1996.

Fisher et al., *Plant Physiol.*, 102(3):1045-1046, 1993.

Fraley et al., *Proc. Natl. Acad. Sci. USA*, 80:4803, 1983.

Geiser et al., *Gene*, 48:109, 1986.

Gordon-Kainm et al., *Plant Cell*, 2:603-618, 1990.

Hamner, In: *The Induction of Flowering: Some Case Histories*, Evans (ed), Cornell Univ. Press, Ithaca, N.Y., 62-89, 1969.

Hartweck et al., *In Vitro Cell. Develop. Bio.*, 24:821-828, 1988.

Japan Pat Appln. 2005080533A2

Jones et al., *Science*, 266:789, 1994.

Knutzon et al., *Proc. Natl. Acad. Sci. USA*, 89:2624, 1992.

Kohno et al., *J Atheroscler Thromb*, 13: 247-255, 2006.

Ladin et al., *Plant Physil.*, 84:35-41, 1987.

Lee et al., *EMBO J.*, 7:1241, 1988.

Logemann et al., *Bio/Technology*, 10:305, 1992.

Manzoni et al., *J. Agric. Food Chem.* 46:2481-2484, 1998.

Manzoni et al., *J. Nutr.* 133:2149-2155, 2003.

Marshall et al., *Theor. Appl. Genet.*, 83:435, 1992.

Martin et al., *Science*, 262:1432, 1993.

Maruyama et al., *J. Agric. Food Chem.* 47:5278-5284, 1999.

Maruyama et al., JAOCS. 79:139, 2002,

Miki et al., *Theor. Appl. Genet.*, 80:449, 1990.

Mindrinos et al., *Cell*, 78:1089, 1994.

Moriyama et al., *Biosci. Biotechnol. Biochem.*, 68(2):352-359, 2004.

Nagano, et al., *J. Agric. Food Chem.* 44 :3484-3488, 1996.

Nakamura et al., *Soy Protein Res* 7: 13-19, 2004.

Nakamura et al., *Soy Protein Res* 8: 1-7, 2005.

Nielsen et al., In: *Cellular and molecular biology of plant seed development*, Larkins and Vasil IK (Eds)., Kluwer Academic Publishers, Dordrecht, The Netherlands, 151-220, 1997.

Nielsen et al., *Plant Cell.*, 1:313-328; 1989.

Nishi et al., *J. Nutr.*, 133(2):352-357, 2003.

PCT Appln. US93/06487

PCT Appln. WO93/19181

PCT Appln. WO96/30517

Poehlman and Sleper, In: *Breeding Field Crops*, Iowa State University Press, Ames, 1995.

Przibila et al., *Plant Cell*, 3:169, 1991.

Rickert, et al. *J. Fd Sci.* 69:303, 2004.

Salleh, et al. *Biosci. Biotech. Biochem.* 68:1091, 2004.

Shah et al., *Science*, 233:478, 1986.

Shanmugasundaram and Tsou, *Crop Sci.*, 18:598-601, 1978.

Shen et al. *J Appl Microbiol* 102: 283-289, 2007

Shibles et al., In:*Crop Physiology, Some Case Histories*, Evans (ed), Cambridge Univ. Press, Cambridge, England, 51-189, 1975.

Shiroza et al., *J. Bacteol.*, 170:810, 1988.

Simmonds, In: *Principles of crop improvement*, Longman, Inc., NY, 369-399, 1979.

Sneep and Hendriksen, In: *Plant breeding perspectives*, Wageningen (ed), Center for Agricultural Publishing and Documentation, 1979.

Søgaard et al., *J. Biol. Chem.*, 268(30):22480-22484, 1993.

Stalker et al., *Science*, 242:419-423, 1988.

Steinmetz et al., *Mol. Gen. Genet.*, 20:220, 1985.

Tezuka et al., *J. Agric. Food Chem.*, 48 :1111-1117, 2000.

Tezuka et al., *J. Agric. Food Chem.*, 52 :1693-1699, 2004.

Tsukada et al. *Japan J. Breed.* 36: 390-400, 1986.

United States Department of Agriculture, *Oilseeds: World Markets and Trade, Foreign Agricultural Service Circular Series*, FOP 7-08, 2008.

Utsumi, In: *Advances in Food and Nutrition Research*, Kinsella (Ed.), 36:89-208, Academic Press, San Diego, Calif., 1992.

Vanden Elzen et al., *Plant Mol. Biol.*, 5:299, 1985.

Wright et al., *Plant Cell Reports*, 5:150-154, 1986.

Yamauchi et al., *Food Rev. Int.* 7: 283-322, 1991.

Zuo et al., *World J Gastroenterol* 11: 5801-5806, 2005.

What is claimed is:

1. A method of producing a soybean plant capable of yielding seeds comprising an increased β-conglycinin α'-subunit content as compared to a typical soybean plant, wherein the α-subunit level and the α'-subunit level in the β-conglycinin trimer are in the ratio of between 0.6 and 0.9, comprising:
    (a) screening at least two soybean seeds for an increased β-conglycinin α'-subunit content as compared to a typical soybean plant;
    (b) selecting a seed having the increased β-conglycinin α'-subunit content as compared to a typical soybean plant, wherein the α-subunit level and the α'-subunit level in the β-conglycinin trimer are in the ratio of between 0.6 and 0.9; and
    (c) growing said selected seed to a flowering plant.

2. The method of claim 1, wherein each of said at least two soybean seeds has PI88188 in its pedigree.

3. The method of claim 1, further comprising the steps of:
    (a) crossing said flowering plant to a second soybean plant to form a population; and
    (b) selecting and growing at least one progeny seed having an increased β-conglycinin α'-subunit content as compared to a typical soybean plant, wherein the α-subunit level and the α'-subunit level in the β-conglycinin trimer are in the ratio of between 0.6 and 0.9.

4. A method of producing a soybean plant capable of yielding seeds comprising an increased β-conglycinin α'-subunit content as compared to a typical soybean plant, wherein the α-subunit level and the α'-subunit level in the β-conglycinin trimer are in the ratio of between 0.6 and 0.9, comprising:
    (a) crossing a first soybean plant with increased β-conglycinin α'-subunit content as compared to a typical soybean plant in its seed, wherein the α-subunit level and the α'-subunit level in the β-conglycinin trimer are in the ratio of between 0.6 and 0.9, with a second soybean plant to form a seed population;
    (b) screening said seed population for the increased β-conglycinin α'-subunit content as compared to a typical soybean plant in the seed protein; and
    (c) selecting and growing at least one seed having the increased β-conglycinin α'-subunit content as compared to a typical soybean plant in the seed protein, wherein the α-subunit level and the α'-subunit level in the β-conglycinin trimer are in the ratio of between 0.6 and 0.9.

5. A method of plant breeding, comprising:
    (a) crossing a glycinin-null plant with a plant capable of yielding seeds comprising an increased β-conglycinin α'-subunit content as compared to a typical soybean plant in the seed protein, wherein the α-subunit level and the α'-subunit level in the β-conglycinin trimer are in the ratio of between 0.6 and 0.9; and
    (b) selecting a progeny seed comprising an α'-subunit content higher than that of either of its parents, wherein the α-subunit level and the α'-subunit level in the β-conglycinin trimer are in the ratio of between 0.6 and 0.9.

6. The method of claim 5, wherein a plant grown from the progeny seed selected in (b) is capable of yielding seeds comprising an increased β-conglycinin α'-subunit content as compared to a typical soybean plant in the seed protein, wherein the α-subunit level and the α'-subunit level in the β-conglycinin trimer are in the ratio of between 0.6 and 0.9.

7. The method of claim 6, wherein said progeny seed further comprises a glycinin content of from about 1% to about 20% of the total protein and a substantially unchanged level of the β-subunit of β-conglycinin.

8. The method of claim 7, wherein said progeny seed comprises a β-conglycinin trimer in which the a-subunit level and the α'-subunit level are in the ratio of between 0.6 and 0.8.

9. A method of detecting the presence of a soybean seed in a population of seed with a glycinin content of from about 1% to about 20% of the total protein and increased β-conglycinin α'-subunit content as compared to a typical soybean plant in the seed protein, wherein the α-subunit level and the α'-subunit level in the β-conglycinin trimer are in the ratio of between 0.6 and 0.9, comprising:
  (a) obtaining a population of soybean seed; and
  (b) detecting in said population the presence of a seed with a glycinin content of from about 1% to about 20% of the total protein and increased β-conglycinin α'-subunit content as compared to a typical soybean plant in the seed protein, wherein the α-subunit level and the α'-subunit level in the β-conglycinin trimer are in the ratio of between 0.6 and 0.9.

10. The method of claim 9, wherein the detection method comprises SDS-PAGE (Sodium Dodecyl Sulfate PolyAcrylamide Gel Electrophoresis) analysis, Western blot analysis, capillary electrophoresis (CE) or Enzyme-Linked ImmunoSobent Assay (ELISA).

* * * * *